US012681490B2

(12) United States Patent
Zhao et al.

(10) Patent No.: US 12,681,490 B2
(45) Date of Patent: Jul. 14, 2026

(54) PATH PLANNING METHOD AND APPARATUS FOR TOMATO INSPECTION ROBOT, DEVICE, MEDIUM, AND PRODUCT

(71) Applicants: ZHEJIANG UNIVERSITY OF SCIENCE & TECHNOLOGY, Hangzhou City (CN); ZHEJIANG UNIVERSITY, Hangzhou City (CN)

(72) Inventors: Yun Zhao, Hangzhou City (CN); Fubo Li, Hangzhou City (CN); Xing Xu, Hangzhou City (CN); Yong He, Hangzhou City (CN); Bingquan Chu, Hangzhou City (CN); Na Wu, Hangzhou City (CN)

(73) Assignees: ZHEJIANG UNIVERSITY OF SCIENCE & TECHNOLOGY; ZHEJIANG UNIVERSITY

( * ) Notice: Subject to any disclaimer, the term of this patent is extended or adjusted under 35 U.S.C. 154(b) by 35 days.

(21) Appl. No.: 19/027,557

(22) Filed: Jan. 17, 2025

(65) Prior Publication Data

US 2026/0104703 A1 Apr. 16, 2026

(30) Foreign Application Priority Data

Oct. 12, 2024 (CN) .......................... 202411420476.0

(51) Int. Cl.
| | |
|---|---|
| *G01C 21/00* | (2006.01) |
| *G01C 21/20* | (2006.01) |
| *G01N 33/02* | (2006.01) |
| *G05D 1/246* | (2024.01) |
| *G05D 1/622* | (2024.01) |
| *G05D 105/80* | (2024.01) |
| *G05D 107/20* | (2024.01) |

(52) U.S. Cl.
CPC ............ *G05D 1/246* (2024.01); *G01C 21/20* (2013.01); *G01N 33/025* (2013.01); *G05D 1/622* (2024.01); *G05D 2105/80* (2024.01); *G05D 2107/21* (2024.01)

(58) Field of Classification Search
CPC .... G05D 1/246; G05D 1/622; G05D 2105/80; G05D 2107/21; G01C 21/20; G01N 33/025
See application file for complete search history.

(56) References Cited

U.S. PATENT DOCUMENTS

| | | | | |
|---|---|---|---|---|
| 2019/0179325 | A1* | 6/2019 | Deng | ................... A47L 11/4011 |
| 2024/0049637 | A1* | 2/2024 | Vandike | ............ A01D 41/1278 |
| 2025/0295050 | A1* | 9/2025 | Rublee | ................... G05D 1/243 |

* cited by examiner

*Primary Examiner* — Ian Jen
(74) *Attorney, Agent, or Firm* — Tutunjian & Bitetto, P.C.

(57) ABSTRACT

Provided are a path planning method and apparatus for a tomato inspection robot. The method includes updating a weight of a heuristic function under a previous iteration ordinal number based on a cost of a positive node under a current iteration ordinal number. A positive heuristic function value set and a negative heuristic function value set are calculated. A positive node and a negative node under a next iteration ordinal number is determined. If there is no obstacle on a direct connection path between the positive node and the negative node under the next iteration ordinal number, backward tracing is performed from the positive node under the next iteration ordinal number to a start point and from the negative node under the next iteration ordinal number to an end point to obtain a planned path. If there is an obstacle, a next iteration is entered.

19 Claims, 13 Drawing Sheets

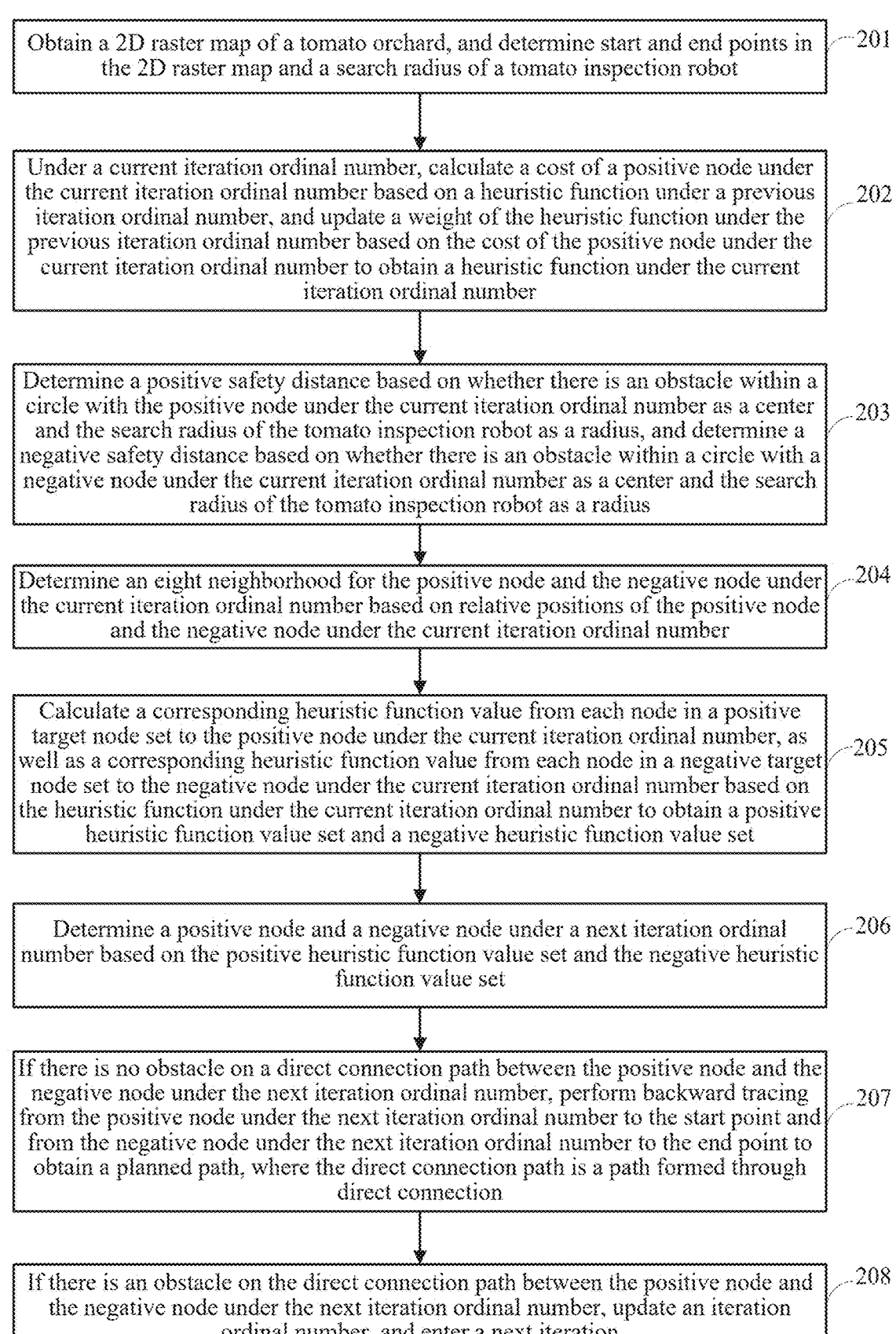

Obtain a 2D raster map of a tomato orchard, and determine start and end points in the 2D raster map and a search radius of a tomato inspection robot ⟋201

Under a current iteration ordinal number, calculate a cost of a positive node under the current iteration ordinal number based on a heuristic function under a previous iteration ordinal number, and update a weight of the heuristic function under the previous iteration ordinal number based on the cost of the positive node under the current iteration ordinal number to obtain a heuristic function under the current iteration ordinal number ⟋202

Determine a positive safety distance based on whether there is an obstacle within a circle with the positive node under the current iteration ordinal number as a center and the search radius of the tomato inspection robot as a radius, and determine a negative safety distance based on whether there is an obstacle within a circle with a negative node under the current iteration ordinal number as a center and the search radius of the tomato inspection robot as a radius ⟋203

Determine an eight neighborhood for the positive node and the negative node under the current iteration ordinal number based on relative positions of the positive node and the negative node under the current iteration ordinal number ⟋204

Calculate a corresponding heuristic function value from each node in a positive target node set to the positive node under the current iteration ordinal number, as well as a corresponding heuristic function value from each node in a negative target node set to the negative node under the current iteration ordinal number based on the heuristic function under the current iteration ordinal number to obtain a positive heuristic function value set and a negative heuristic function value set ⟋205

Determine a positive node and a negative node under a next iteration ordinal number based on the positive heuristic function value set and the negative heuristic function value set ⟋206

If there is no obstacle on a direct connection path between the positive node and the negative node under the next iteration ordinal number, perform backward tracing from the positive node under the next iteration ordinal number to the start point and from the negative node under the next iteration ordinal number to the end point to obtain a planned path, where the direct connection path is a path formed through direct connection ⟋207

If there is an obstacle on the direct connection path between the positive node and the negative node under the next iteration ordinal number, update an iteration ordinal number, and enter a next iteration ⟋208

PATH PLANNING METHOD AND APPARATUS FOR TOMATO INSPECTION ROBOT, DEVICE, MEDIUM, AND PRODUCT

CROSS REFERENCE TO RELATED APPLICATION

This patent application claims the benefit and priority of Chinese Patent Application No. 202411420476.0, filed with the China National Intellectual Property Administration on Oct. 12, 2024, the disclosure of which is incorporated by reference herein in its entirety as part of the present application.

TECHNICAL FIELD

The present disclosure relates to the field of path planning for mobile robots, and in particular, to a path planning method and apparatus for a tomato inspection robot, a device, a medium, and a product.

BACKGROUND

In modern agricultural production, it is crucial to accurately monitor and manage a crop in a timely manner. Especially in tomato production, the ability to quickly detect a growth problem and perform corresponding processing can effectively improve a yield and quality of the crop. However, traditional crop inspection usually relies on manual inspection, which not only consumes a lot of manpower and material resources, but also has low efficiency and is easily affected by subjective factors.

To overcome these shortcomings, the artificial intelligence technology is developed to make a revolutionary improvement to path planning for a mobile robot. Especially in agricultural applications, the artificial intelligence technology can be used to enable the mobile robot to intelligently complete an entire autonomous driving process during tomato inspection, thereby reducing manual dependence and enhancing an automation level of the system. However, when an original A* algorithm is used for the path planning, planning efficiency and accuracy are low.

SUMMARY

An objective of the present disclosure is to provide a path planning method and apparatus for a tomato inspection robot, a device, a medium, and a product, which can improve efficiency and accuracy of path planning.

To achieve the above objective, the present disclosure provides the following technical solutions.

According to a first aspect, the present disclosure provides a path planning method for a tomato inspection robot, includes obtaining a two-dimensional (2D) raster map of a tomato orchard, and determining start and end points in the 2D raster map and a search radius of the tomato inspection robot.

Under a current iteration ordinal number, calculating a cost of a positive node under the current iteration ordinal number based on a heuristic function under a previous iteration ordinal number, and updating a weight of the heuristic function under the previous iteration ordinal number based on the cost of the positive node under the current iteration ordinal number to obtain a heuristic function under the current iteration ordinal number, where the cost is a sum of a corresponding heuristic function value from the positive node under the current iteration ordinal number to a negative node under the current iteration ordinal number, a corresponding heuristic function value from the positive node under the current iteration ordinal number to the end point, and a corresponding heuristic function value from the positive node under the current iteration ordinal number to the start point; the heuristic function is a weighted sum of a Euclidean distance and a diagonal distance between two nodes; and a positive node under an initial iteration ordinal number is the start point, and a negative node under the initial iteration ordinal number is the end point.

A positive safety distance is determined based on whether there is an obstacle within a circle with the positive node under the current iteration ordinal number as a center and the search radius of the tomato inspection robot as a radius, and determining a negative safety distance based on whether there is an obstacle within a circle with the negative node under the current iteration ordinal number as a center and the search radius of the tomato inspection robot as a radius.

An eight neighborhood for the positive node and the negative node under the current iteration ordinal number is determined based on relative positions of the positive node and the negative node under the current iteration ordinal number.

A corresponding heuristic function value is calculated from each node in a positive target node set to the positive node under the current iteration ordinal number, as well as a corresponding heuristic function value from each node in a negative target node set to the negative node under the current iteration ordinal number based on the heuristic function under the current iteration ordinal number to obtain a positive heuristic function value set and a negative heuristic function value set, where the positive target node set includes all nodes whose distances from the positive node under the current iteration ordinal number are greater than the positive safety distance in the eight neighborhood of the positive node under the current iteration ordinal number, and the negative target node set includes all nodes whose distances from the negative node under the current iteration ordinal number are greater than the negative safety distance in the eight neighborhood of the negative node under the current iteration ordinal number.

A positive node and a negative node are determined under a next iteration ordinal number based on the positive heuristic function value set and the negative heuristic function value set.

If there is no obstacle on a direct connection path between the positive node and the negative node under the next iteration ordinal number, performing backward tracing from the positive node under the next iteration ordinal number to the start point and from the negative node under the next iteration ordinal number to the end point to obtain a planned path, where the direct connection path is a path formed through direct connection.

If there is an obstacle on the direct connection path between the positive node and the negative node under the next iteration ordinal number, updating an iteration ordinal number, and entering a next iteration.

According to a second aspect, the present disclosure provides a path planning apparatus for a tomato inspection robot, includes an obtaining module configured to obtain a 2D raster map of a tomato orchard, and determine start and end points in the 2D raster map and a search radius of the tomato inspection robot.

An updating module is configured to: under a current iteration ordinal number, calculate a cost of a positive node under the current iteration ordinal number based on a heuristic function under a previous iteration ordinal number, and update a weight of the heuristic function under the previous iteration ordinal number based on the cost of the positive node under the current iteration ordinal number to obtain a heuristic function under the current iteration ordinal number, where the cost is a sum of a corresponding heuristic function value from the positive node under the current iteration ordinal number to a negative node under the current iteration ordinal number, a corresponding heuristic function value from the positive node under the current iteration ordinal number to the end point, and a corresponding heuristic function value from the positive node under the current iteration ordinal number to the start point; the heuristic function is a weighted sum of a Euclidean distance and a diagonal distance between two nodes; and a positive node under an initial iteration ordinal number is the start point, and a negative node under the initial iteration ordinal number is the end point;

A safety distance determining module is configured to determine a positive safety distance based on whether there is an obstacle within a circle with the positive node under the current iteration ordinal number as a center and the search radius of the tomato inspection robot as a radius, and determine a negative safety distance based on whether there is an obstacle within a circle with the negative node under the current iteration ordinal number as a center and the search radius of the tomato inspection robot as a radius.

An eight neighborhood determining module is configured to determine an eight neighborhood for the positive node and the negative node under the current iteration ordinal number based on relative positions of the positive node and the negative node under the current iteration ordinal number.

A heuristic function value set calculation module is configured to: calculate a corresponding heuristic function value from each node in a positive target node set to the positive node under the current iteration ordinal number, as well as a corresponding heuristic function value from each node in a negative target node set to the negative node under the current iteration ordinal number based on the heuristic function under the current iteration ordinal number to obtain a positive heuristic function value set and a negative heuristic function value set, where the positive target node set includes all nodes whose distances from the positive node under the current iteration ordinal number are greater than the positive safety distance in the eight neighborhood of the positive node under the current iteration ordinal number, and the negative target node set includes all nodes whose distances from the negative node under the current iteration ordinal number are greater than the negative safety distance in the eight neighborhood of the negative node under the current iteration ordinal number;

A module for determining a node under a next iteration ordinal number is configured to determine a positive node and a negative node under the next iteration ordinal number based on the positive heuristic function value set and the negative heuristic function value set.

A planned path determining module is configured to: if there is no obstacle on a direct connection path between the positive node and the negative node under the next iteration ordinal number, perform backward tracing from the positive node under the next iteration ordinal number to the start point and from the negative node under the next iteration ordinal number to the end point to obtain a planned path, where the direct connection path is a path formed through direct connection.

An iteration module is configured to: if there is an obstacle on the direct connection path between the positive node and the negative node under the next iteration ordinal number, update an iteration ordinal number, and enter a next iteration.

According to a third aspect, the present disclosure provides a computer device, including a memory, a processor, and a computer program stored in the memory and executable on the processor, where the processor executes the computer program to implement the above path planning method for a tomato inspection robot.

According to a fourth aspect, the present disclosure provides a computer-readable storage medium, where a computer program is stored thereon, and the computer program is executed by a processor to implement the above path planning method for a tomato inspection robot.

According to a fifth aspect, the present disclosure provides a computer program product, including a computer program, where the computer program is executed by a processor to implement the above path planning method for a tomato inspection robot.

According to specific embodiments provided in the present disclosure, the present disclosure achieves the following technical effects:

The present disclosure provides a path planning method and apparatus for a tomato inspection robot, a device, a medium, and a product. Based on a weighted sum of a Euclidean distance and a diagonal distance between two nodes, a heuristic function value is obtained to balance diagonal and straight-line elements. A weight of a heuristic function is updated in real time based on a cost of a positive node, which can better adapt to path planning needs in different environments. In this way, both a global optimal path and an optimal selection of a local path are considered, thereby enhancing adaptability and efficiency of an algorithm in a complex environment, and improving precision of path planning.

A safety distance is adjusted based on a distance between an obstacle and the positive node as well as a distance between the obstacle and a negative node. This avoids a collision and reduces unnecessary path extension in a path planning process, optimizes a feasible safety distance of a path, and improves efficiency of the path planning.

An eight neighborhood is determined based on relative positions of the positive node and the negative node, which can adapt to different terrains and obstacle distributions, improving the precision of the path planning.

If there is no obstacle on a direct connection path between the positive node and the negative node, backward tracing is performed to obtain a planned path, and point-to-point connection can be performed directly. This can significantly reduce a quantity of nodes in path extension and shorten search time, thus improving the efficiency of the path planning.

BRIEF DESCRIPTION OF THE DRAWINGS

To describe the technical solutions in the embodiments of the present disclosure or in the prior art more clearly, the following briefly describes the accompanying drawings required for the embodiments. Apparently, the accompanying drawings in the following description show merely some embodiments of the present disclosure, and a person of ordinary skill in the art may still derive other accompanying drawings from these accompanying drawings without creative efforts.

FIG. 1 is a flowchart of a path planning method for a tomato inspection robot according to an embodiment of the present disclosure;

DETAILED DESCRIPTION OF THE EMBODIMENTS

Figure 2A:
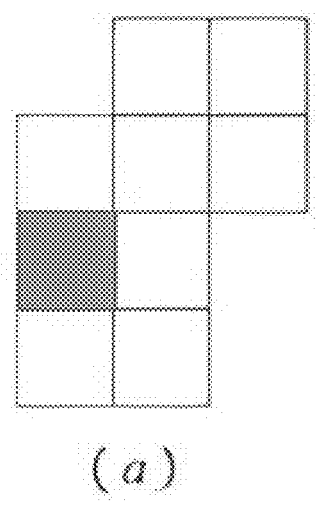
FIGS. 2A-2D are schematic diagrams of eight neighborhood templates corresponding to four quadrants.

The technical solutions in the embodiments of the present disclosure are clearly and completely described below with reference to the accompanying drawings in the embodiments of the present disclosure. Apparently, the described embodiments are only some rather than all of the embodiments of the present disclosure. All other embodiments obtained by a person of ordinary skill in the art based on the embodiments of the present disclosure without creative efforts shall fall within the protection scope of the present disclosure.

To make the above objectives, features, and advantages of the present disclosure more obvious and easier to understand, the present disclosure will be further described in detail with reference to the accompanying drawings and specific implementations.

In an exemplary embodiment, as shown in FIG. 1, a path planning method for a tomato inspection robot is provided. The path planning method is obtained by improving an existing bidirectional A* algorithm and specifically includes the following steps:

Step 201: Obtain a 2D raster map of a tomato orchard, and determine start and end points in the 2D raster map and a search radius of a tomato inspection robot.

Step 202: Under a current iteration ordinal number, calculate a cost of a positive node under the current iteration ordinal number based on a heuristic function under a previous iteration ordinal number, and update a weight of the heuristic function under the previous iteration ordinal number based on the cost of the positive node under the current iteration ordinal number to obtain a heuristic function under the current iteration ordinal number, where the cost is a sum of a corresponding heuristic function value from the positive node under the current iteration ordinal number to a negative node under the current iteration ordinal number, a corresponding heuristic function value from the positive node under the current iteration ordinal number to the end point, and a corresponding heuristic function value from the positive node under the current iteration ordinal number to the start point; the heuristic function is a weighted sum of a Euclidean distance and a diagonal distance between two nodes; and a positive node under an initial iteration ordinal number is the start point, and a negative node under the initial iteration ordinal number is the end point. This step combines the heuristic function defined by the diagonal distance and the Euclidean distance to balance diagonal and straight-line elements to evaluate a cost from a current node to a target node. This improves efficiency and accuracy of path planning compared with an existing bidirectional A* algorithm. Compared with the existing bidirectional A* algorithm, in terms of the cost, the present disclosure no longer solely focuses on the end point, but simultaneously considers the current node in both forward and backward searches, thereby enhancing a global search capability and efficiency of an algorithm. The weight of the heuristic function is dynamically adjusted based on the cost of the positive node under the current iteration ordinal number. Compared with the existing bidirectional A* algorithm, the present disclosure can better adapt to path planning needs in different environments. The heuristic function is adjusted, such that both a global optimal path and an optimal selection of a local path are considered, thereby enhancing adaptability and efficiency of the algorithm in a complex environment.

Step 203: Determine a positive safety distance based on whether there is an obstacle within a circle with the positive node under the current iteration ordinal number as a center and the search radius of the tomato inspection robot as a radius, and determine a negative safety distance based on whether there is an obstacle within a circle with the negative node under the current iteration ordinal number as a center and the search radius of the tomato inspection robot as a radius. Compared with the existing bidirectional A* algorithm, the present disclosure adjusts a safety distance to avoid a collision and reduce unnecessary path extension in a path planning process, thereby optimizing feasibility of a path.

Step 204: Determine an eight neighborhood for the positive node and the negative node under the current iteration ordinal number based on relative positions of the positive node and the negative node under the current iteration ordinal number.

Step 205: Calculate a corresponding heuristic function value from each node in a positive target node set to the positive node under the current iteration ordinal number, as well as a corresponding heuristic function value from each node in a negative target node set to the negative node under the current iteration ordinal number based on the heuristic function under the current iteration ordinal number to obtain a positive heuristic function value set and a negative heuristic function value set, where the positive target node set includes all nodes whose distances from the positive node under the current iteration ordinal number are greater than the positive safety distance in the eight neighborhood of the positive node under the current iteration ordinal number, and the negative target node set includes all nodes whose distances from the negative node under the current iteration ordinal number are greater than the negative safety distance in the eight neighborhood of the negative node under the current iteration ordinal number.

Step 206: Determine a positive node and a negative node under a next iteration ordinal number based on the positive heuristic function value set and the negative heuristic function value set.

Figure 14:
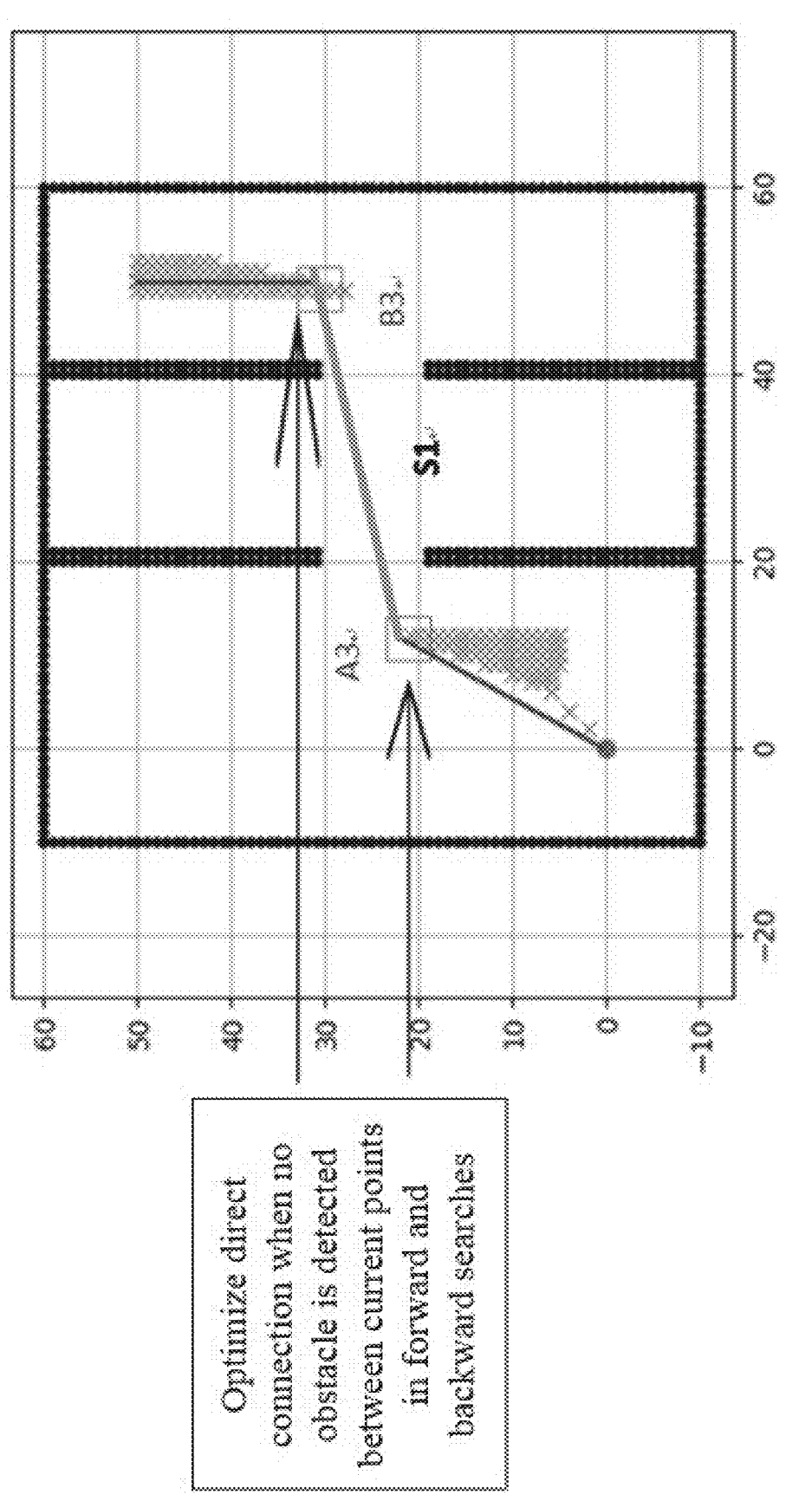
FIG. 14 shows a result of a direct connection path obtained by directly connecting A3 and B3 in actual path planning.

Step 207: If there is no obstacle on a direct connection path between the positive node and the negative node under the next iteration ordinal number, perform backward tracing from the positive node under the next iteration ordinal number to the start point and from the negative node under the next iteration ordinal number to the end point to obtain a planned path, where the direct connection path is a path formed through direct connection. A specific process of determining the direct connection path is to draw a straight line by using a Breasenham algorithm by taking the positive node under the next iteration ordinal number as a start point and the negative node under the next iteration ordinal number as an end point, to obtain the direct connection path. In the existing bidirectional A* algorithm, logic for generating a complete path is to set a position at which points newly generated by ends A and B are both located as an encountering point, and end the extension in a search process. Compared with the existing bidirectional A* algorithm, the present disclosure directly performs point-to-point connection when there is no obstacle between two nodes in a bidirectional search, which can significantly reduce a quantity of nodes in path extension and shorten search time. As shown in FIG. 14, nodes A3 and B3, as the current nodes in the forward and backward searches, optimize the direct connection when no obstacle is detected in a direct connection path between two points (in other words, a line segment S1 does not collide with an obstacle). This strategy improves computational efficiency.

Step 208: If there is an obstacle on the direct connection path between the positive node and the negative node under the next iteration ordinal number, update an iteration ordinal number, and enter a next iteration.

The above steps 201 to 208 can be performed to significantly reduce a quantity of search nodes and execution time of the algorithm, improve efficiency and accuracy of path planning for a mobile robot in a complex agricultural environment, and more effectively plan a travel route of the mobile robot, thereby achieving more efficient crop monitoring and management.

Figure 16:
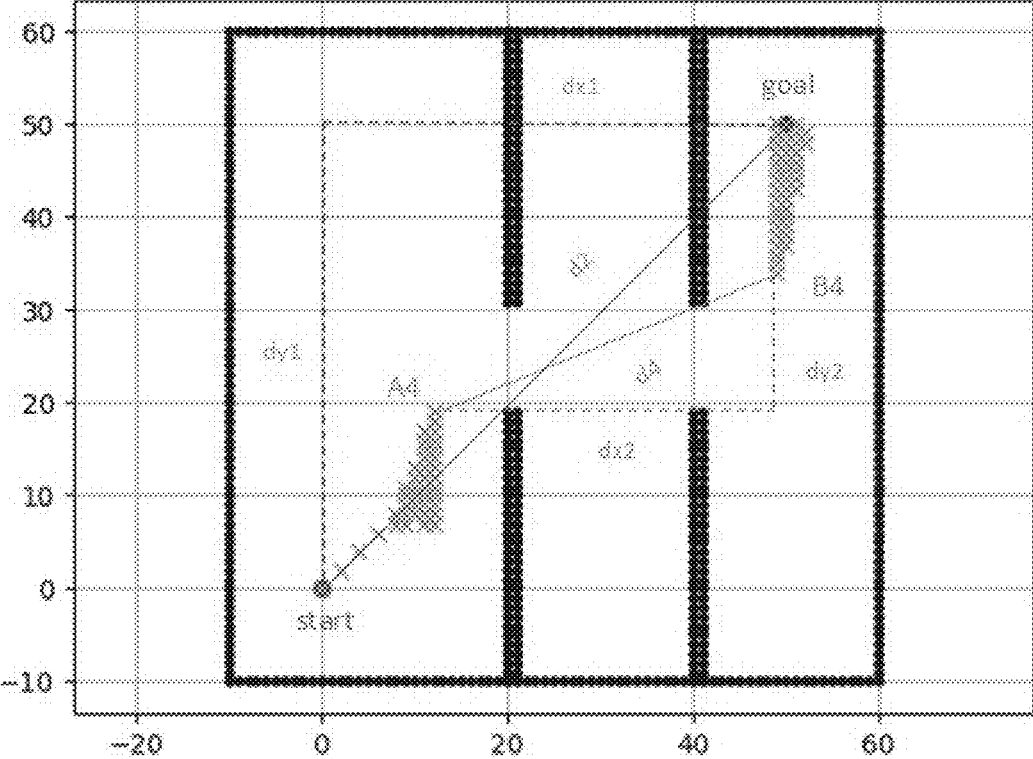
FIG. 16 is a schematic diagram of adjusting a weight of a heuristic function.
Figure 17:
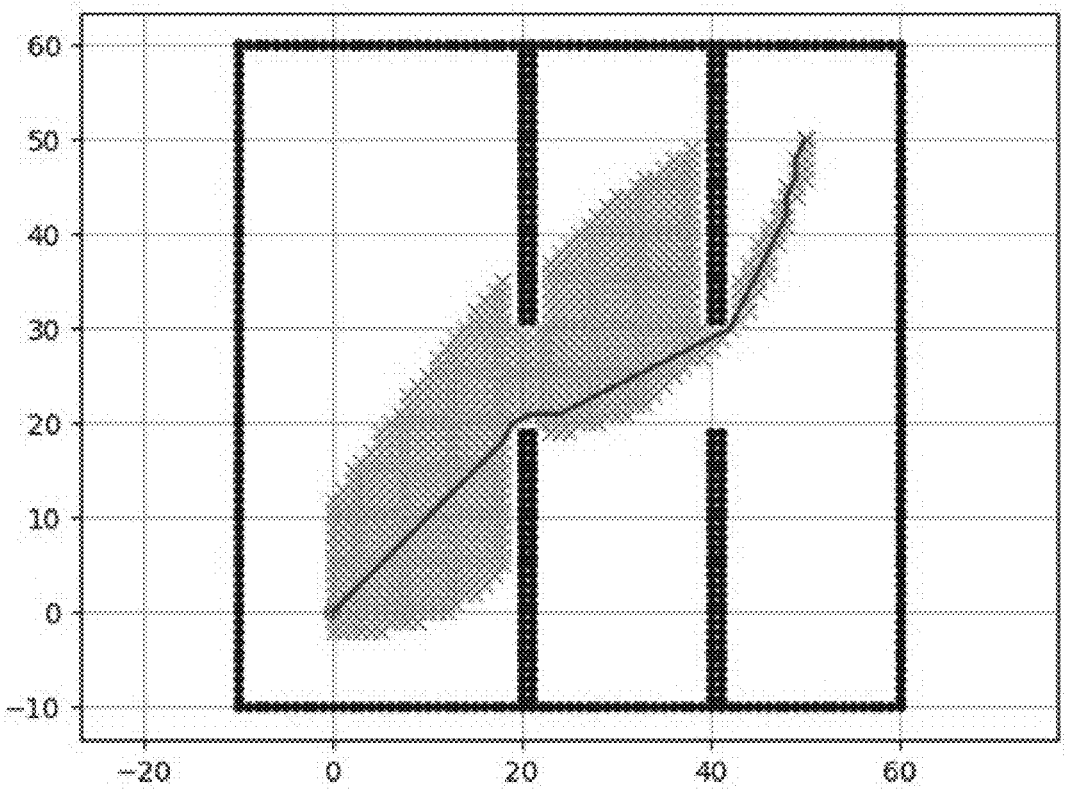
FIG. 17 is a schematic diagram corresponding to a planned path obtained through processing by using an A* algorithm in Table 4.
Figure 18:
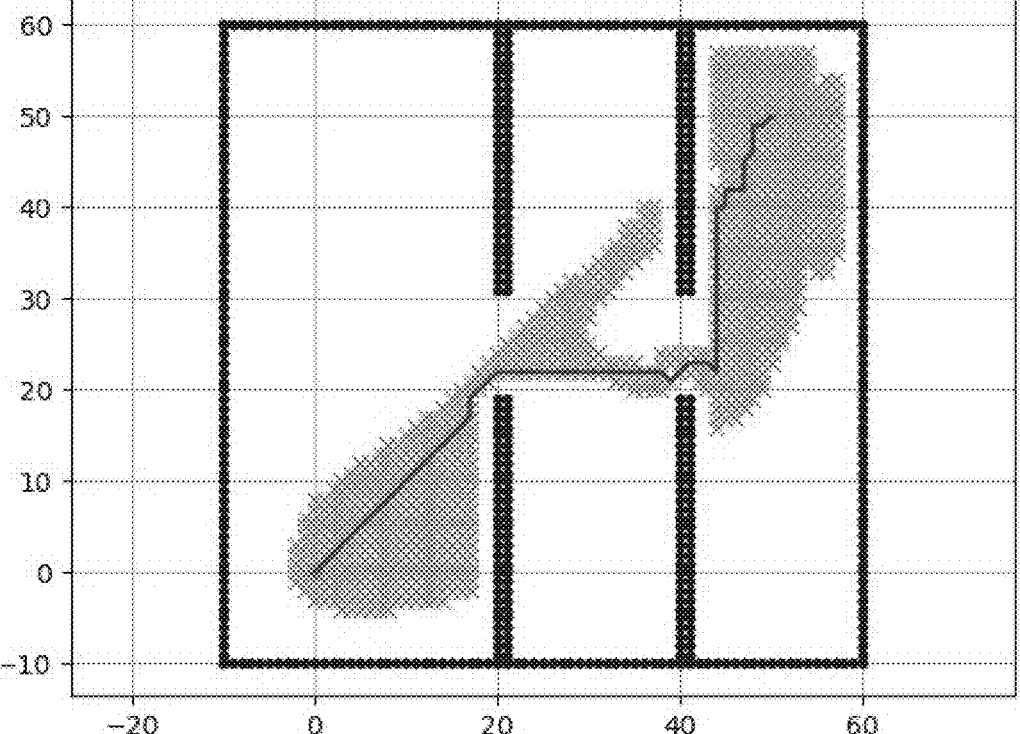
FIG. 18 is a schematic diagram corresponding to a planned path obtained through processing by using an existing bidirectional A* algorithm in Table 4.
Figure 19:
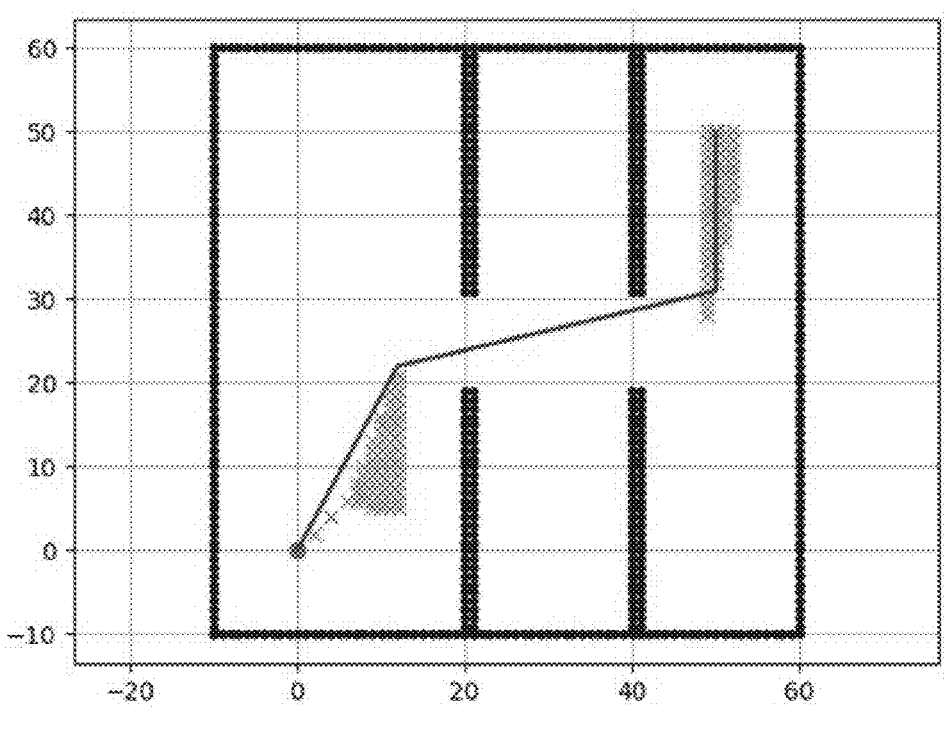
FIG. 19 is a schematic diagram corresponding to a planned path obtained through processing by using a path planning method provided in the present disclosure in Table 4.

In another exemplary embodiment of the present disclosure, the heuristic function is as follows:

$d = w1 \times d1 + w2 \times d2 + w3 \times 2.828 \times \min(dx,dy) + w4 \times 2.236 \times \min(dx,dy)$, where d represents the heuristic function value, d1 represents a diagonal distance between a $1^{st}$ node and a $2^{nd}$ node, d2 represents a Euclidean distance between the $1^{st}$ node and the $2^{nd}$ node, dx represents an absolute value of a difference between an abscissa of the $1^{st}$ node and an abscissa of the $2^{nd}$ node, dy represents an absolute value of a difference between an ordinate of the $1^{st}$ node and an ordinate of the $2^{nd}$ node, $\min(dx, dy)$ represents a minimum value between the dx and the dy, w1 represents a first weight, w2 represents a second weight, w3 represents a third weight, and w4 represents a fourth weight. As shown in FIG. 16, the application of the heuristic function combines the diagonal distance and the Euclidean distance. A cost of the start point is a heuristic function value from the start point to a goal point, and a cost of a point A4 is a heuristic function value from the point A4 to a point B4, a heuristic function value from the point A4 to the start point, and a heuristic function value from the point A4 to the goal point.

In another exemplary embodiment of the present disclosure, the determining a positive safety distance based on whether there is an obstacle within a circle with the positive node under the current iteration ordinal number as a center and the search radius of the tomato inspection robot as a radius includes:

If there is an obstacle within the circle with the positive node under the current iteration ordinal number as the center and the search radius of the tomato inspection robot as the radius, the positive safety distance is increased (to five times an entity radius of the robot).

Figure 15:
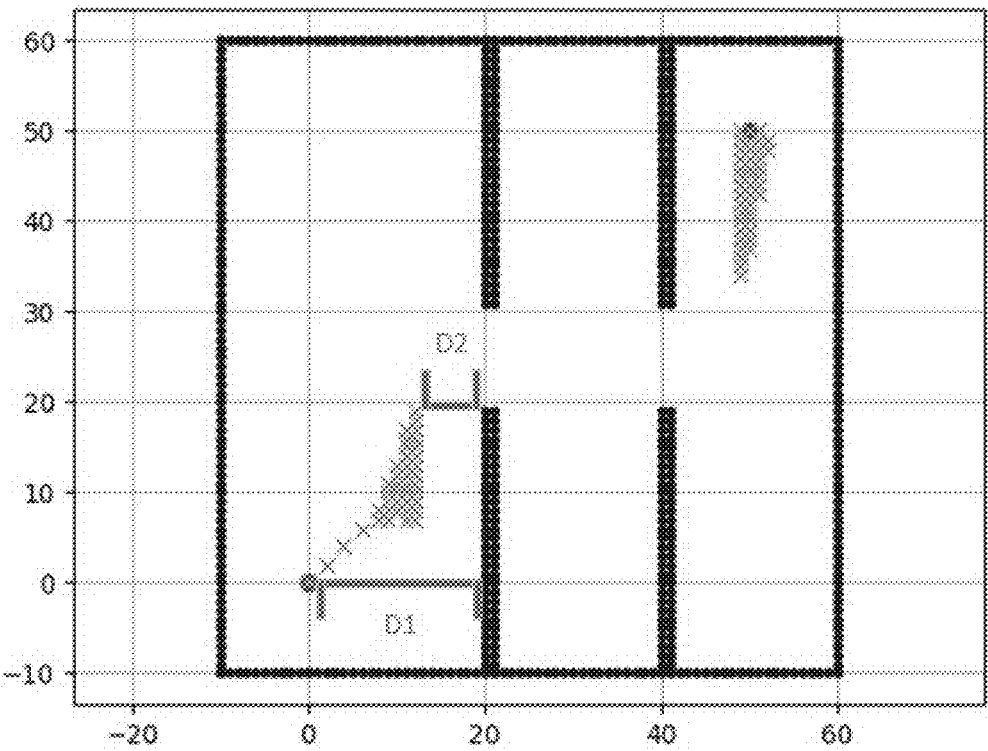
FIG. 15 is a schematic diagram of dynamically adjusting a safety distance.

If there is no obstacle within the circle with the positive node under the current iteration ordinal number as the center and the search radius of the tomato inspection robot as the radius, the positive safety distance is decreased (to one times the entity radius of the robot). As shown in FIG. 15, the safety distance is dynamically adjusted in real time by measuring a distance from a current positive node to a nearest obstacle (D1) and a distance from a current negative node to the obstacle (D2). The safety distance is adaptively adjusted based on 1 to 5 times the entity radius of the robot. When the distance is short, a larger safety distance is used, and when the distance is long, a smaller safety distance is used, aiming to ensure safety in a region with dense obstacles while optimizing path efficiency. This aims to ensure that the robot does not collide with any obstacle and reduce a quantity of expansion points. FIG. 15 shows use of the smaller safety distance for the D1 and the larger safety distance for the D2.

In another exemplary embodiment of the present disclosure, the determining a negative safety distance based on whether there is an obstacle within a circle with the negative node under the current iteration ordinal number as a center and the search radius of the tomato inspection robot as a radius specifically includes:

if there is an obstacle within the circle with the negative node under the current iteration ordinal number as the center and the search radius of the tomato inspection robot as the radius, increasing the negative safety distance; or if there is no obstacle within the circle with the negative node under the current iteration ordinal number as the center and the search radius of the tomato inspection robot as the radius, decreasing the negative safety distance.

In another exemplary embodiment of the present disclosure, the determining an eight neighborhood for the positive node and the negative node under the current iteration ordinal number based on relative positions of the positive node and the negative node under the current iteration ordinal number specifically includes:

establishing a positive coordinate system with the positive node under the current iteration ordinal number as an origin;

obtaining the eight neighborhood for the positive node under the current iteration ordinal number based on an eight neighborhood template corresponding to a quadrant in which the negative node under the current iteration ordinal number is located in the positive coordinate system;

establishing a negative coordinate system with the negative node under the current iteration ordinal number as an origin; and obtaining the eight neighborhood for the negative node under the current iteration ordinal number based on an eight neighborhood template corresponding to a quadrant in which the positive node under the current iteration ordinal number is located in the negative coordinate system, where compared with an eight neighborhood in the existing bidirectional A* algorithm, an appropriate eight neighborhood is selected based on a quadrant in which the current node is located in the present disclosure to adapt to different terrains and obstacle distributions.

Figure 12:
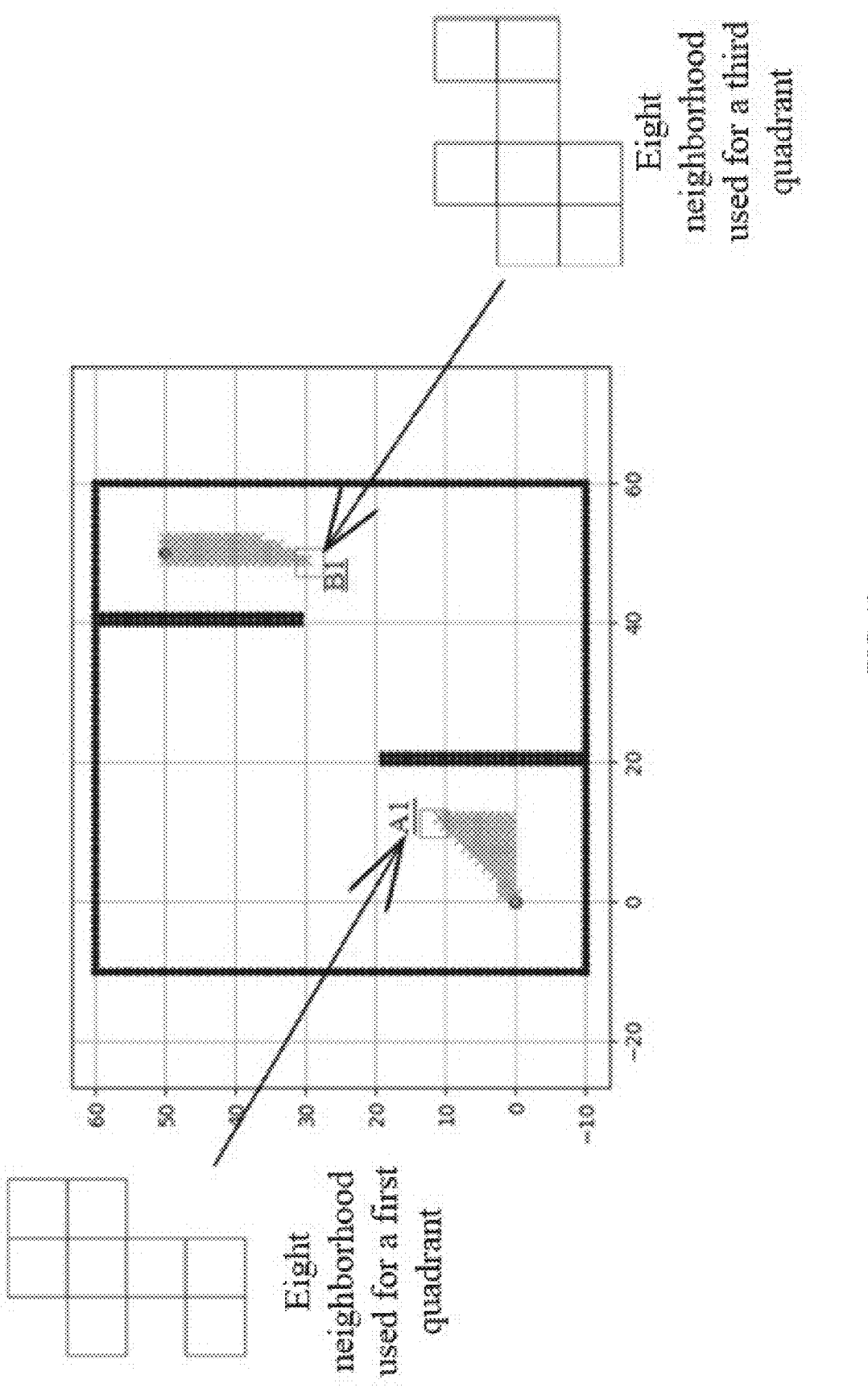
FIG. 12 shows an eight neighborhood template used in actual path planning when a node A1 and a node B1 are respectively located in third and first quadrants.
Figure 13:
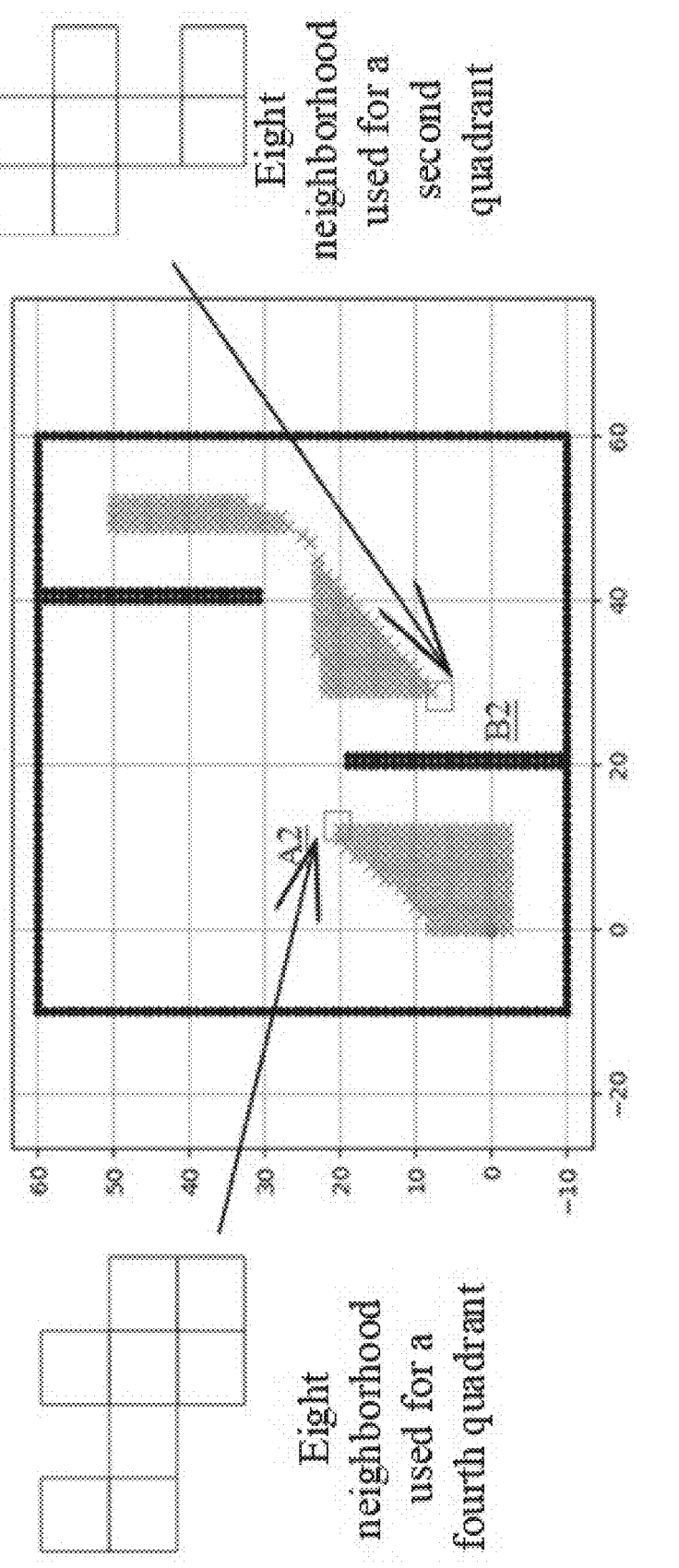
FIG. 13 shows an eight neighborhood template used in actual path planning when a node A2 and a node B2 are respectively located in second and fourth quadrants.

Specifically, in an embodiment shown in FIG. 12, because a point B1 is in a first quadrant of a coordinate system with a point A1 as an origin, an eight neighborhood template corresponding to the first quadrant is used for an eight neighborhood of the point A1. Similarly, the point B1 uses an eight neighborhood template corresponding to a third quadrant. The quadrant-based neighborhood selection not only optimizes a search path, but also reduces a computational overhead. Further, as shown in FIG. 13, a search strategy for a point A2 is selected in a corresponding domain based on a fourth quadrant in which the other party is located, and a search strategy for a point B2 is selected in a corresponding domain based on a second quadrant in which the other party is located, thereby improving search efficiency.

Figure 2B:
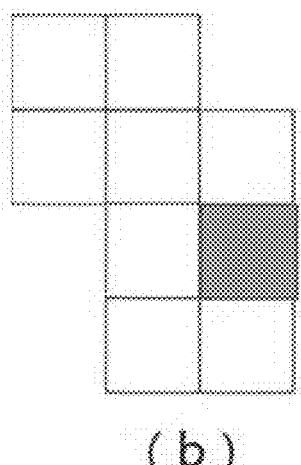
Figure 2C:
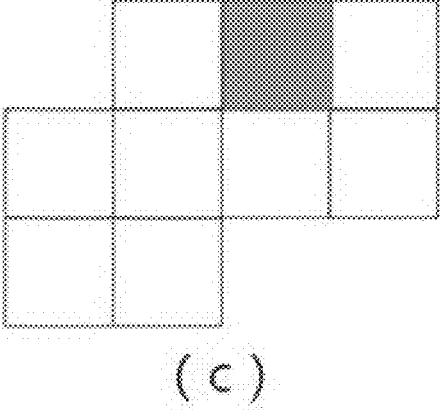
Figure 2D:
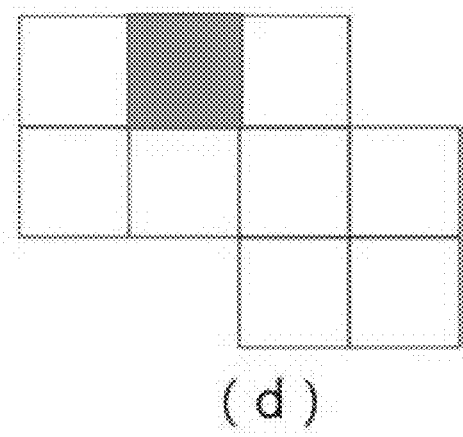
Figure 3:
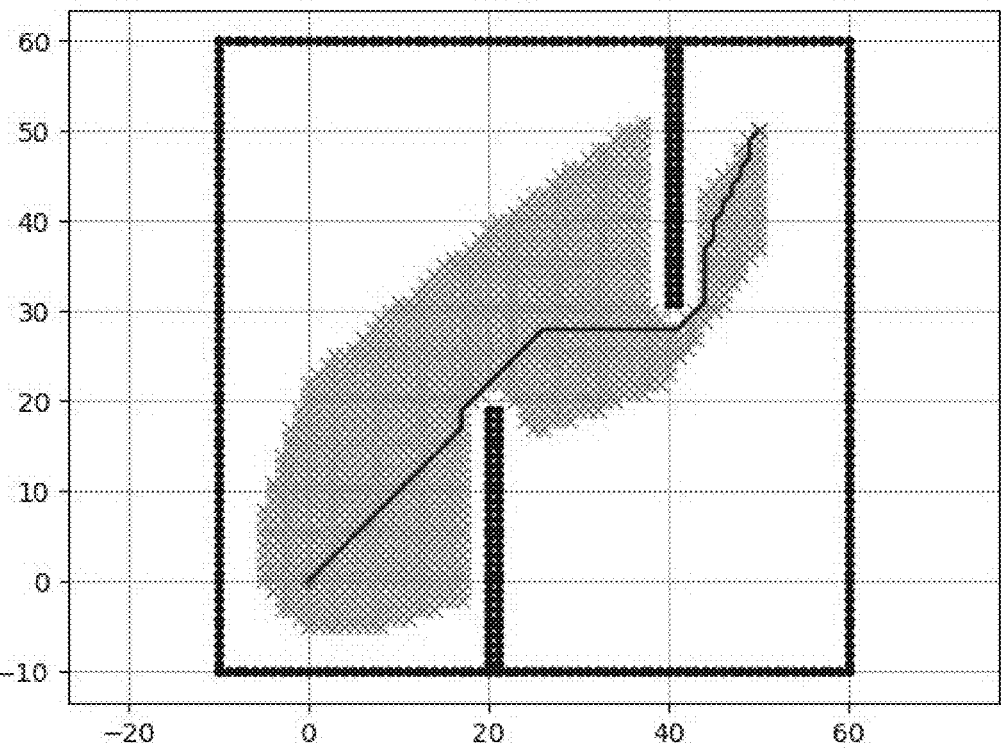
FIG. 3 is a schematic diagram corresponding to a planned path obtained through processing by using an A* algorithm in Table 1.
Figures 4, 5:
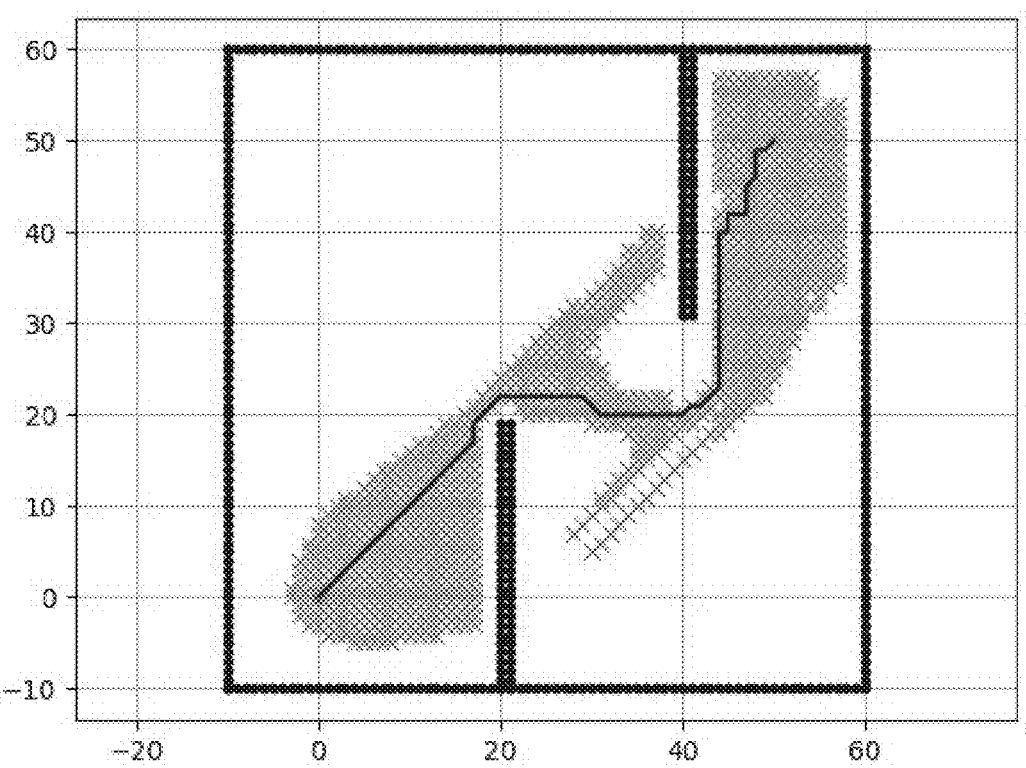
FIG. 4 is a schematic diagram corresponding to a planned path obtained through processing by using an existing bidirectional A* algorithm in Table 1.
FIG. 5 is a schematic diagram corresponding to a planned path obtained through processing by using a path planning method provided in the present disclosure in Table 1.
Figure 6:
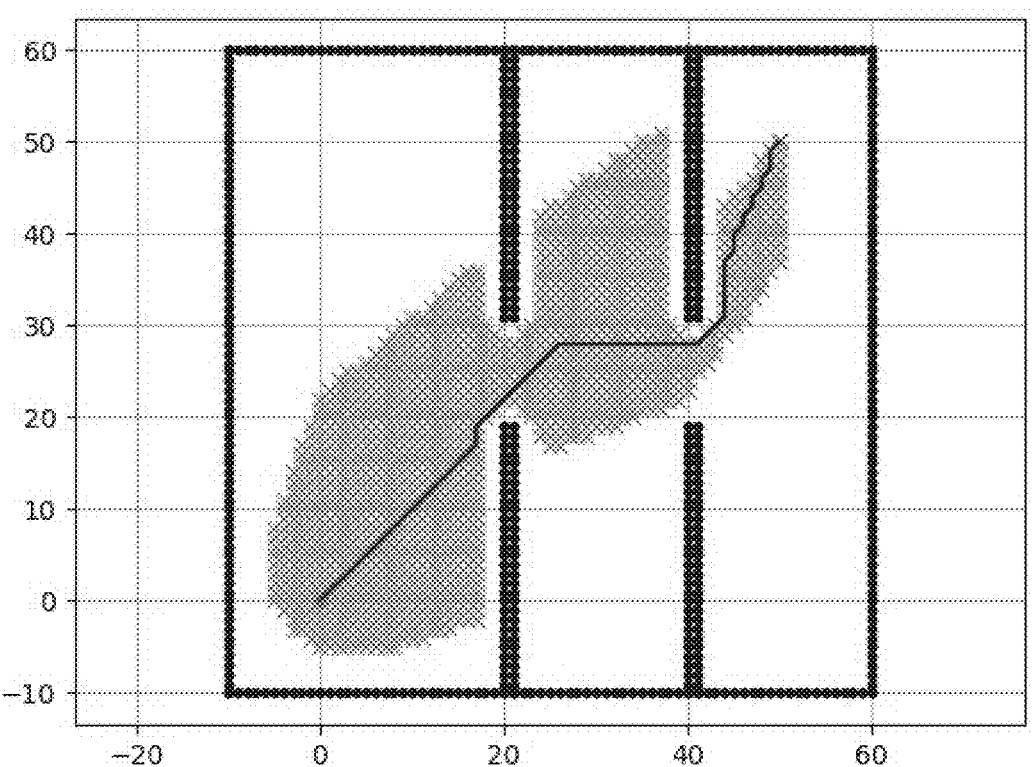
FIG. 6 is a schematic diagram corresponding to a planned path obtained through processing by using an A* algorithm in Table 2.
Figure 7:
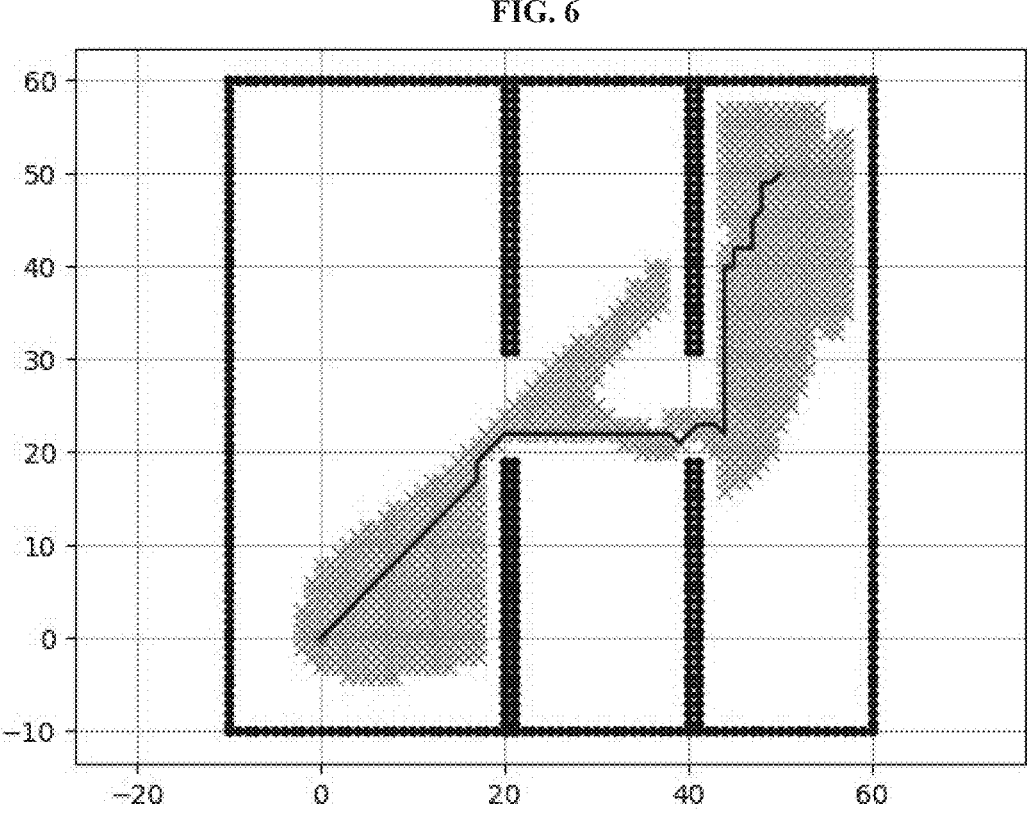
FIG. 7 is a schematic diagram corresponding to a planned path obtained through processing by using an existing bidirectional A* algorithm in Table 2.
Figure 8:
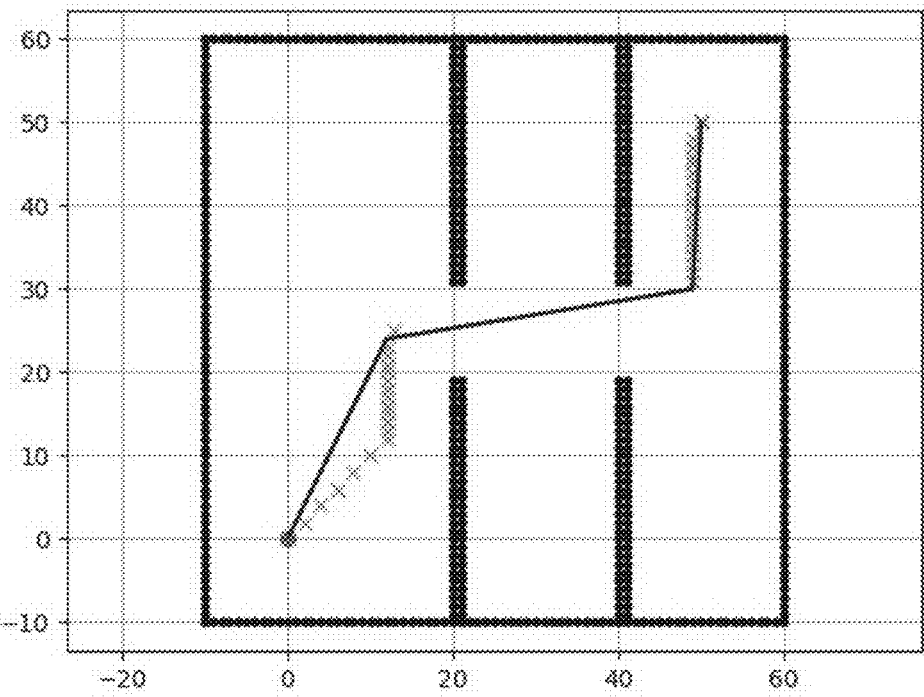
FIG. 8 is a schematic diagram corresponding to a planned path obtained through processing by using a path planning method provided in the present disclosure in Table 2.
Figure 9:
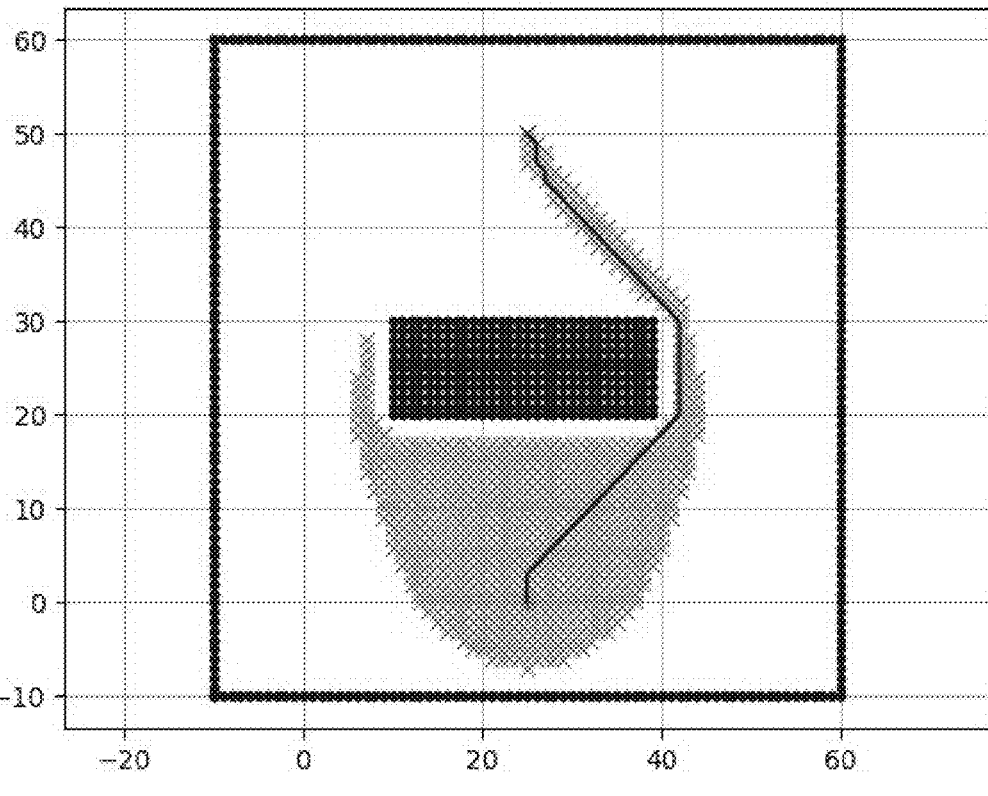
FIG. 9 is a schematic diagram corresponding to a planned path obtained through processing by using an A* algorithm in Table 3.
Figure 10:
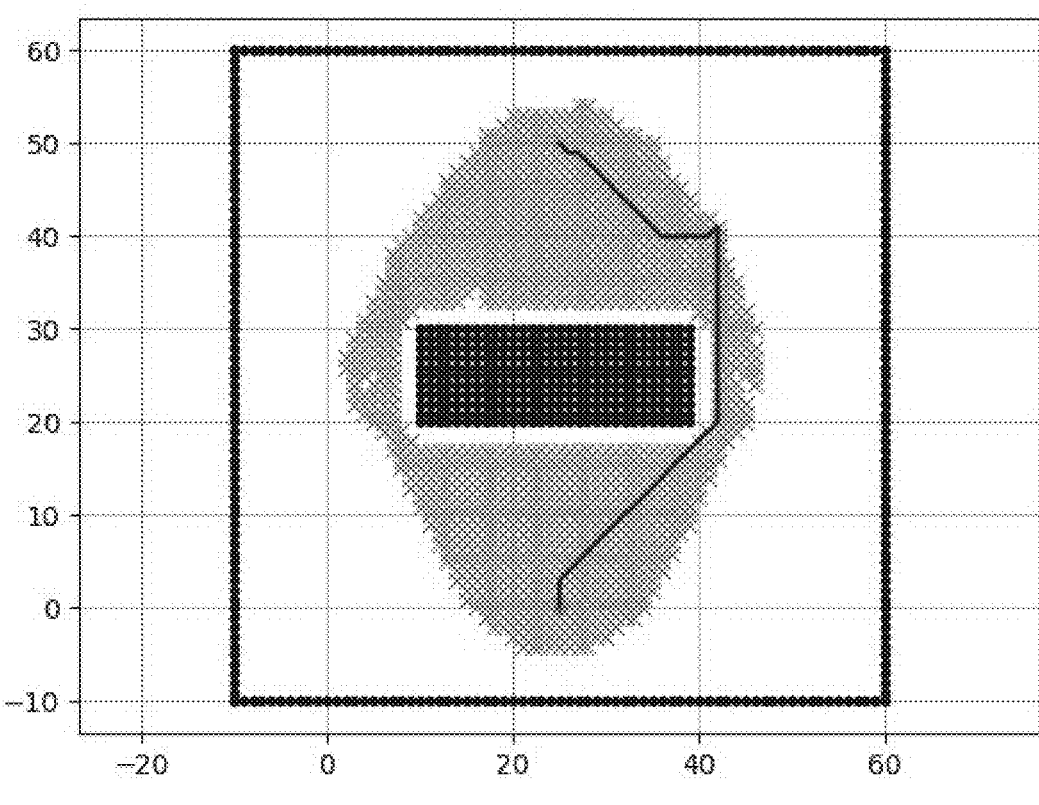
FIG. 10 is a schematic diagram corresponding to a planned path obtained through processing by using an existing bidirectional A* algorithm in Table 3.
Figure 11:
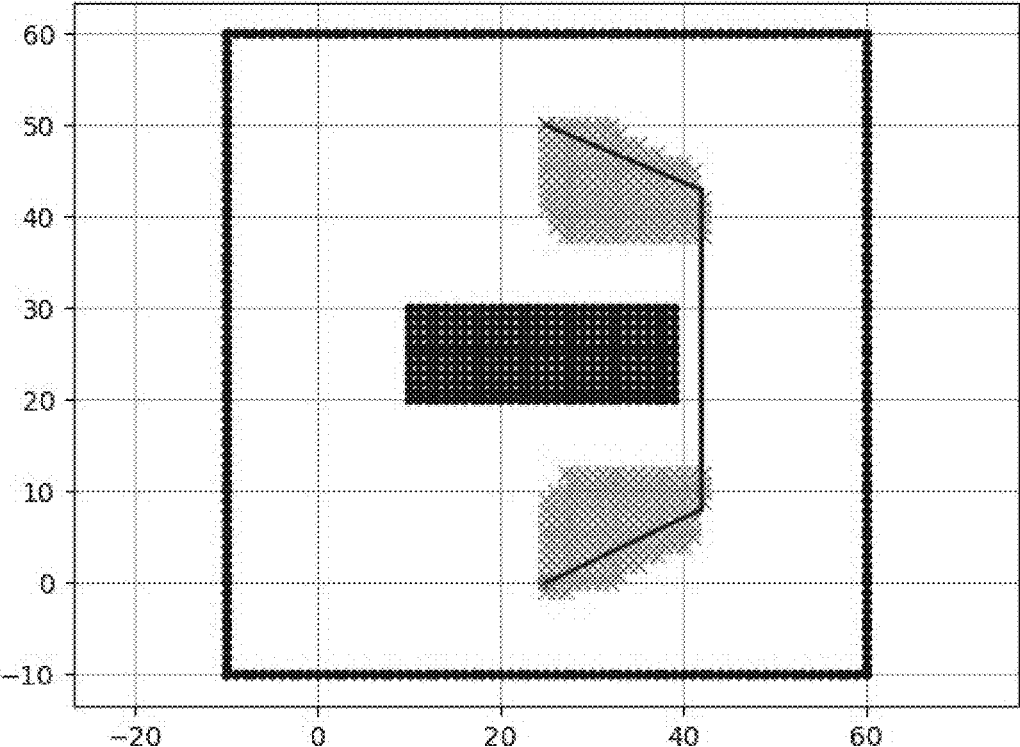
FIG. 11 is a schematic diagram corresponding to a planned path obtained through processing by using a path planning method provided in the present disclosure in Table 3.

In a practical application, the eight neighborhood corresponding to the first quadrant is shown in FIG. 2A, an eight neighborhood corresponding to the second quadrant is shown in FIG. 2B, the eight neighborhood corresponding to the third quadrant is shown in FIG. 2C, and an eight neighborhood corresponding to the fourth quadrant is shown in FIG. 2D. An eight neighborhood corresponding to a quadrant is constructed to replace a traditional eight neighborhood, such that a search is more directional, thereby improving algorithm efficiency. Additionally, as a search range expands, the path becomes more directional, avoiding some traps that a traditional algorithm cannot avoid.

In another exemplary embodiment of the present disclosure, the calculating a corresponding heuristic function value from each node in a positive target node set to the positive node under the current iteration ordinal number, as well as a corresponding heuristic function value from each node in a negative target node set to the negative node under the current iteration ordinal number based on the heuristic function under the current iteration ordinal number to obtain a positive heuristic function value set and a negative heuristic function value set specifically includes:

calculating the corresponding heuristic function value from each node in the positive target node set to the positive node under the current iteration ordinal based on the heuristic function under the current iteration ordinal number to obtain the positive heuristic function value set; and calculating the corresponding heuristic function value from each node in the negative target node set to the negative node under the current iteration ordinal number based on the heuristic function under the current iteration ordinal number to obtain the negative heuristic function value set.

In another exemplary embodiment of the present disclosure, the determining a positive node and a negative node under a next iteration ordinal number based on the positive heuristic function value set and the negative heuristic function value set specifically includes:

determining a node in a positive target node set corresponding to a minimum heuristic function value in the positive heuristic function value set as the positive node under the next iteration ordinal number; and determining a node in a negative target node set corresponding to a minimum heuristic function value in the negative heuristic function value set as the negative node under the next iteration ordinal number.

In another exemplary embodiment of the present disclosure, the performing backward tracing from the positive node under the next iteration ordinal number to the start point and from the negative node under the next iteration ordinal number to the end point to obtain a planned path specifically includes:

performing the backward tracing from the positive node under the next iteration ordinal number to the start point and from the negative node under the next iteration ordinal number to the end point to obtain a preliminary path; and smoothing the preliminary path to obtain the planned path.

The present disclosure provides a more specific embodiment to illustrate an effect of the path planning method for a tomato inspection robot provided in the above embodiments:

Step 1: Perform map preprocessing and parameter initialization.

Input data: 2D raster maps of four tomato orchards, which are shown in FIG. 3 to FIG. 11 and FIG. 17 to FIG. 19.

Steps for processing any one of the maps are as follows:

Step A1: Initialize a start point, an end point, and open sets (open_set_A and open_set_B) and closed sets (closed_set_A and closed_set_B) in two directions (a forward direction (from the start point to the end point) and a backward direction (from the end point to the start point)), save the start point and its corresponding to-be-searched point to the start point to the open_set_A, and save the end point and its corresponding to-be-searched point to the open_set_B.

Step A2: Calculate a maximum coordinate boundary and a minimum coordinate boundary of the map and an obstacle position, initialize a raster size to 1 (grid resolution), and initialize a search radius (which is determined based on a map size, for example, is 10 when the map is a 70×70 square) of a tomato inspection robot and a radius of the robot to 2.

Output data: initialized path planning environment and parameters (the map size, the obstacle position, the raster size (grid resolution), positions of the start point and the end point, a robot size, and the search radius that is of the tomato inspection robot and determined based on the map size).

Step 2: Enable a bidirectional search.

Input data: data output in the step 1.

Processing steps are as follows:

Step B1: Construct a heuristic function. An eight-directional distance that combines a diagonal distance and a Euclidean distance and fits a greedy search direction is used as the heuristic function: $d=0.25×d1+0.375×d2+0.25×d3+0.125×d4$, where $d1=1.414×min(dx,dy)$, $d2=abs(dx-dy)$, $d3=2.828×min(dx,dy)$, $d4=2.236×min(dx,dy)$, $dx=abs(n1.x-n2.x)$, $dy=abs(n1.y-n2.y)$, $abs( )$ represents an operation of taking an absolute value, $n1.x$ represents an abscissa of a node $n1$, $n2.x$ represents an abscissa of a node $n2$, $n1.y$ represents an ordinate of the node $n1$, and $n2.y$ represents an ordinate of the node $n2$. An original eight-directional distance in an existing bidirectional A* algorithm uses $d1+d2$ as the heuristic function.

Step B2: Use the improved heuristic function to calculate a cost of a positive node current_A under a current iteration ordinal number, namely a sum of a heuristic function value from the current_A to a point current_B, a heuristic function value from the current_A to the end point, and a heuristic function value from the current_A to the start point.

Step B3: If the cost is greater than the search radius of the tomato inspection robot, a weight sum of the heuristic function is 2. If the cost is not greater than the search radius of the tomato inspection robot, the weight sum of the heuristic function is 0.8.

Step B4: Dynamically adjust a safety distance based on a density of obstacles around current nodes (the current_A and the current_B). A circle is drawn by taking the current_A as a center and the search radius of the tomato inspection robot as a radius. If there is an obstacle inside the circle, a larger positive safety distance is used. If there is no obstacle inside the circle, a smaller positive safety distance is used. A circle is drawn by taking the current_B as a center and the search radius of the tomato inspection robot as a radius. If there is an obstacle inside the circle, a larger negative safety distance is used. If there is no obstacle inside the circle, a smaller negative safety distance is used. The safety distance is adaptively adjusted based on 1 to 5 times an entity radius of the robot, aiming to ensure safety in a region with dense obstacles while optimizing path efficiency.

Step B5: Establish a positive coordinate system with the current_A as an origin, and obtain a neighboring node of the current_A based on an eight neighborhood template corresponding to a quadrant in which the current_B is located in the positive coordinate system; and establish a negative coordinate system with the current_B as an origin, and obtain a neighboring node of the current_B based on an eight neighborhood template corresponding to a quadrant in which the current_B is located in the negative coordinate system.

Step B6: Draw a circle by taking the current_A as a center and a positive safety distance as a radius, and delete a neighboring node of the current_A inside the circle to obtain a positive target node set; draw a circle by taking the current_B as a center and a negative safety distance as a radius, and delete a neighboring node of the current_B inside the circle to obtain a negative target node set; calculate a corresponding heuristic function value from each node in the positive target node set to the current_A based on a weight-updated heuristic function, determine a node with a minimum heuristic function value as a positive node under a next iteration ordinal number, delete the positive node from the open_set_A, and then add the positive node to the closed_set_A; and calculate a corresponding heuristic function value from each node in the negative target node set to the current_B based on the weight-updated heuristic function, determine a node with a minimum heuristic function value as a negative node under the next iteration ordinal number, delete the negative node from the open_set_B, and, then add the negative node to the closed_set_B.

Output data: updated open and closed sets after each iteration, and the positive node and the negative node under the next iteration ordinal number.

Step 3: Perform straight-line sight line inspection, and optimize direct connection of a path.

Input data: the positive node and the negative node that are under the next iteration ordinal number and obtained in the step 2.

A process is as follows:

Step C1: Use a straight-line algorithm to check whether the positive node and the negative node under the next iteration ordinal number can be directly connected.

Specific steps of a direct-connection algorithm are as follows:

1. Obtain position information of the positive node and the negative node under the next iteration ordinal number, and label the positive node under the next iteration ordinal number as the start point and the negative node under the next iteration ordinal number as the end point.

2. Starting from the start point, move towards a direction of the end point based on a step of 1, and check for any obstacle on a point reached after each step of movement.

3. During the movement, if there is an obstacle, stop the movement, and return "unable to be directly connected". If there is no obstacle, it means that the start point and the end point can be directly connected.

Step C2: If it is detected that the direct connection can be performed, directly connect the positive node and the negative node under the next iteration ordinal number to obtain a direct connection path, determine the positive node and the negative node under the next iteration ordinal number as encountering points, and proceed to the step 3.

Step C3: If no direct connection path is detected, return to the step 2.

Output data: the direct connection path and the identified encountering points.

Step 4: Generate and optimize a path.

Input data: the encountering points and the direct connection path that are obtained in the step 3.

A process is as follows:

Step D3: Perform backward tracing from the encountering point to the start point and the end point to generate a preliminary path.

Step D4: Apply another smoothing method to the preliminary path to reduce turns and improve continuity of the path, so as to obtain a planned path.

Output data: the planned path.

Step 5: Perform analysis and adjustment.

Input data: the planned path generated in the step 4.

A process is as follows:

The 2D raster map of the tomato orchard in the step 1 is processed by using an A* algorithm and the existing bidirectional A* algorithm to generate the planned path.

1. Calculate a length for the planned path generated by using the A* algorithm, the existing bidirectional A* algorithm, and the step 4 (the path planning method for a tomato inspection robot proposed in the present disclosure) separately (perform iteration forward from the end point, calculate a length from each discrete point in the path to a previous point until the start point is reached, and add all lengths to obtain the path length).

2. Calculate a quantity of turns for the planned path generated by using the A* algorithm, the existing bidirectional A* algorithm, and the step 4 (the path planning method for a tomato inspection robot proposed in the present disclosure) separately (set an initial quantity of turns to 0 and a turn threshold to 0.1 radians, namely 5.73 degrees, use a dot product formula and a vector length to calculate a cosine value of an included angle between vectors of two points, use an acos function to calculate an angle based on the cosine value, and increase the quantity of turns by 1 if the angle is greater than a threshold).

3. Calculate time separately used by the A* algorithm, the existing bidirectional A* algorithm, and the step 4 (the path planning method for a tomato inspection robot proposed in the present disclosure) to generate the planned path (that is, record time 1 at the beginning of path planning, record time 2 after the planning is completed, and obtain execution time, where execution time=time 2–time 1).

Output data: performance analysis results shown in Table 1 to Table 3.

TABLE 1

| Model | Search time (ms) | Path length | Quantity of search nodes | Quantity of turns |
| --- | --- | --- | --- | --- |
| A* | 11.3324 | 79.50 | 1354 | 16 |
| Bidirectional A* | 4.4471 | 88.18 | 1046 | 17 |
| Ours | 1.1090 | 84.99 | 190 | 2 |

TABLE 2

| Model | Search time (ms) | Path length | Quantity of search nodes | Quantity of turns |
| --- | --- | --- | --- | --- |
| A* | 10.6076 | 79.50 | 1293 | 16 |
| Bidirectional A* | 3.9821 | 88.77 | 968 | 15 |
| Ours | 0.4196 | 84.34 | 40 | 2 |

TABLE 3

| Model | Search time (ms) | Path length | Quantity of search nodes | Quantity of turns |
| --- | --- | --- | --- | --- |
| A* | 5.0831 | 64.08 | 795 | 7 |
| Bidirectional A* | 6.5966 | 69.60 | 1326 | 6 |
| Ours | 2.3289 | 72.17 | 390 | 2 |

TABLE 4

| Model | Search time (ms) | Path length | Quantity of search nodes | Quantity of turns |
| --- | --- | --- | --- | --- |
| A* | 4.8329 | 74.94 | 926 | 9 |
| Bidirectional A* | 1.3766 | 82.08 | 356 | 22 |
| Ours | 0.4365 | 83.11 | 132 | 2 |

Based on Table 1 to Table 4, FIG. 3 to FIG. 11, and FIG. 17 to FIG. 19, it can be seen that the path planning method for a tomato inspection robot proposed in the present disclosure reduces the quantity of search nodes, the search time of the algorithm, and the quantity of turns, improving planning efficiency and accuracy of the mobile robot.

Based on the same inventive concept, the embodiments of the present disclosure also provide a path planning apparatus for a tomato inspection robot to implement the above path planning method for a tomato inspection robot. A problem-solving implementation solution provided by the apparatus is similar to the implementation solution described in the above method. Therefore, for following specific limitations on one or more embodiments of the path planning apparatus for a tomato inspection robot, reference may be made to the above limitations on the path planning method for a tomato inspection robot, and details are not described herein again.

In an exemplary embodiment, a path planning apparatus for a tomato inspection robot is provided, including:

an obtaining module configured to obtain a 2D raster map of a tomato orchard, and determine start and end points in the 2D raster map and a search radius of the tomato inspection robot;

an updating module configured to: under a current iteration ordinal number, calculate a cost of a positive node under the current iteration ordinal number based on a heuristic function under a previous iteration ordinal number, and update a weight of the heuristic function under the previous iteration ordinal number based on the cost of the positive node under the current iteration ordinal number to obtain a heuristic function under the current iteration ordinal number, where the cost is a sum of a corresponding heuristic function value from the positive node under the current iteration ordinal number to a negative node under the current iteration ordinal number, a corresponding heuristic function value from the positive node under the current iteration ordinal number to the end point, and a corresponding heuristic function value from the positive node under the current iteration ordinal number to the start point; the heuristic function is a weighted sum of a Euclidean distance and a diagonal distance between two nodes; and a positive node under an initial iteration ordinal number is the start point, and a negative node under the initial iteration ordinal number is the end point;

a safety distance determining module configured to determine a positive safety distance based on whether there is an obstacle within a circle with the positive node under the current iteration ordinal number as a center and the search radius of the tomato inspection robot as a radius, and determine a negative safety distance based on whether there is an obstacle within a circle with the negative node under the current iteration ordinal number as a center and the search radius of the tomato inspection robot as a radius;

an eight neighborhood determining module configured to determine an eight neighborhood for the positive node and the negative node under the current iteration ordinal number based on relative positions of the positive node and the negative node under the current iteration ordinal number;

a heuristic function value set calculation module configured to: calculate a corresponding heuristic function value from each node in a positive target node set to the positive node under the current iteration ordinal number, as well as a corresponding heuristic function value from each node in a negative target node set to the negative node under the current iteration ordinal number based on the heuristic function under the current iteration ordinal number to obtain a positive heuristic function value set and a negative heuristic function value set, where the positive target node set includes all nodes whose distances from the positive node under the current iteration ordinal number are greater than the positive safety distance in the eight neighborhood of the positive node under the current iteration ordinal number, and the negative target node set includes all nodes whose distances from the negative node under the current iteration ordinal number are greater than the negative safety distance in the eight neighborhood of the negative node under the current iteration ordinal number;

a module for determining a node under a next iteration ordinal number configured to determine a positive node and a negative node under the next iteration ordinal number based on the positive heuristic function value set and the negative heuristic function value set;

a planned path determining module configured to: if there is no obstacle on a direct connection path between the positive node and the negative node under the next iteration ordinal number, perform backward tracing from the positive node under the next iteration ordinal number to the start point and from the negative node under the next iteration ordinal number to the end point to obtain a planned path, where the direct connection path is a path formed through direct connection; and an iteration module configured to: if there is an obstacle on the direct connection path between the positive node and the negative node under the next iteration ordinal number, update an iteration ordinal number, and enter a next iteration.

Figure 20:
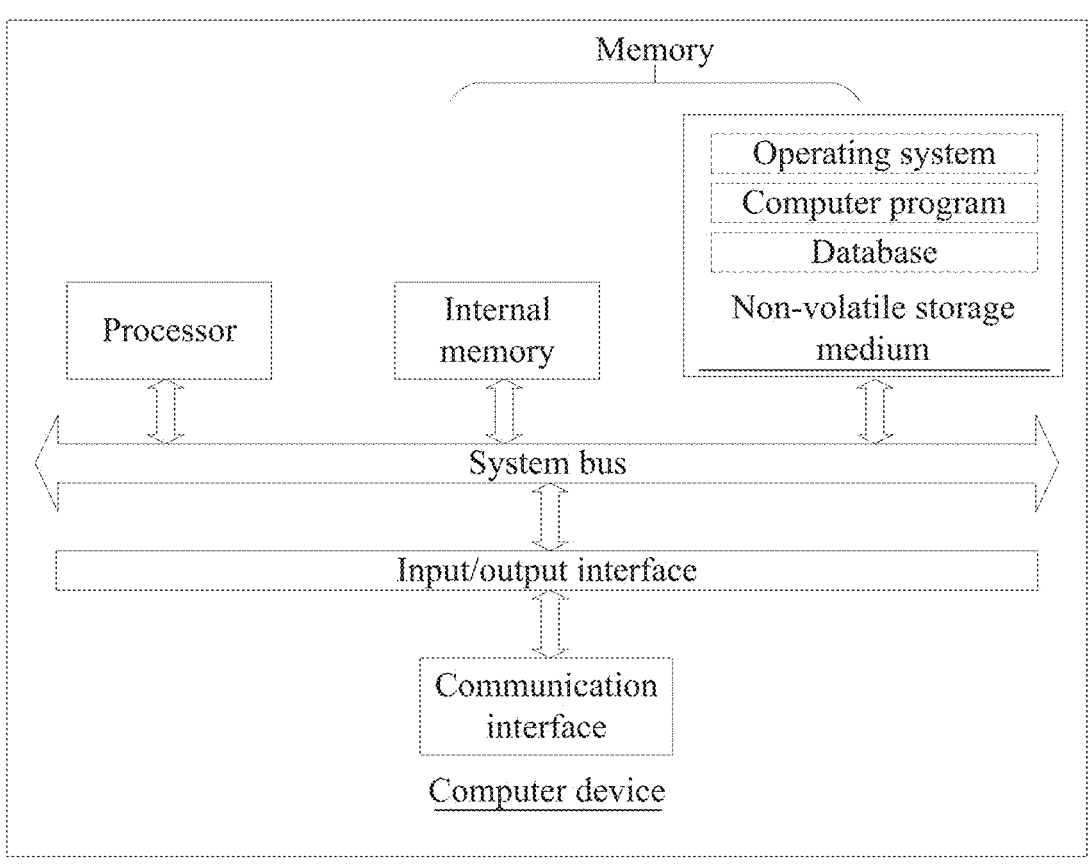
FIG. 20 is a schematic structural diagram of a computer device according to an embodiment of the present disclosure.

In an exemplary embodiment, a computer device is provided. The computer device may be a server or a terminal, and an internal structure thereof may be as shown in FIG. 20. The computer device includes a processor, a memory, an input/output (I/O) interface, and a communication interface. The processor, the memory, and the I/O interface are connected through a system bus. The communication interface is connected to the system bus through the I/O interface. The processor of the computer device is configured to provide computing and control capabilities. The memory of the computer device includes a non-volatile storage medium and an internal memory. The non-volatile storage medium stores an operating system, a computer program, and a database. The internal memory provides an environment for running the operating system and the computer program in the non-volatile storage medium. The database of the computer device is configured to store path planning data of a tomato inspection robot. The I/O interface of the computer device is configured to exchange information between the processor and an external device. The communication interface of the computer device is configured to connect to and communicate with an external terminal through a network. The computer program is executed by the processor to implement the path planning method for a tomato inspection robot.

Those skilled in the art may understand that the structure shown in FIG. 20 is only a block diagram of a partial structure related to the solutions of the present disclosure and does not constitute a limitation on a computer device to which the solutions of the present disclosure are applied. Specifically, the computer device may include more or less components than those shown in the figure, or combine some components, or have different component arrangements. In an exemplary embodiment, a computer device is provided, including a memory and a processor. The memory stores a computer program, and the processor executes the computer program to implement the above method embodiments.

In an exemplary embodiment, a computer-readable storage medium is provided. The computer-readable storage medium stores a computer program, and the computer program is executed by a processor to implement the above method embodiments.

In an exemplary embodiment, a computer program product is provided, including a computer program. The computer program is executed by a processor to implement the above method embodiments.

Those of ordinary skill in the art may understand that all or some of the procedures in the method of the above embodiments may be implemented by a computer program instructing related hardware. The computer program may be stored in a non-volatile computer-readable storage medium. When the computer program is executed, the procedures in the embodiments of the above method may be performed. Any reference to a memory, a storage, a database, or other media used in the embodiments of the present disclosure may include at least one of a non-volatile memory and a volatile memory. The non-volatile memory may include a read-only memory (ROM), a magnetic tape, a floppy disk, a flash memory, an optical memory, a high-density embedded non-volatile memory, a resistive random access memory (ReRAM), a magnetoresistive random access memory (MRAM), a ferroelectric random access memory (FRAM), a phase change memory (PCM), a graphene memory, and the like. The volatile memory may include a random access memory (RAM) or an external cache memory. As an illustration rather than a limitation, the RAM may be in various forms, such as a static random access memory (SRAM) or a dynamic random access memory (DRAM).

The database in the embodiments of the present disclosure may include at least one of a relational database and a non-relational database. The non-relational database may include a blockchain-based distributed database, but is not limited thereto. The processor in the embodiments of the present disclosure may be a general processor, a central processing unit (CPU), a graphics processor, a digital signal processor (DSP), a programmable logic device, a data processing logic device based on quantum computing, and the like, but is not limited thereto.

The technical characteristics of the above embodiments can be employed in arbitrary combinations. To provide a concise description of these embodiments, all possible combinations of all the technical characteristics of the above embodiments may not be described; however, these combinations of the technical characteristics should be construed as falling within the scope defined by the specification as long as no contradiction occurs.

Specific examples are used herein for illustration of the principles and implementations of the present disclosure. The description of the above embodiments is used to help illustrate the method of the present disclosure and the core principles thereof. In addition, those of ordinary skill in the art can make various modifications in terms of specific implementations and scope of application in accordance with the teachings of the present disclosure. In conclusion, the content of the specification shall not be construed as a limitation to the present disclosure.

What is claimed is:

1. A path planning method for a tomato inspection robot, comprising:

obtaining a two-dimensional (2D) raster map of a tomato orchard, and determining start and end points in the 2D raster map and a search radius of the tomato inspection robot;

under a current iteration ordinal number, calculating a cost of a positive node under the current iteration ordinal number based on a heuristic function under a previous iteration ordinal number, and updating a weight of the heuristic function under the previous iteration ordinal number based on the cost of the positive node under the current iteration ordinal number to obtain a heuristic function under the current iteration ordinal number, wherein the cost is a sum of a corresponding heuristic function value from the positive node under the current iteration ordinal number to a negative node under the current iteration ordinal number, a corresponding heuristic function value from the positive node under the current iteration ordinal number to the end point, and a corresponding heuristic function value from the positive node under the current iteration ordinal number to the start point; the heuristic function is a weighted sum of a Euclidean distance and a diagonal distance between two nodes; and a positive node under an initial iteration ordinal number is the start point, and a negative node under the initial iteration ordinal number is the end point;

determining a positive safety distance based on whether there is an obstacle within a circle with the positive node under the current iteration ordinal number as a center and the search radius of the tomato inspection robot as a radius, and determining a negative safety distance based on whether there is an obstacle within a circle with the negative node under the current iteration ordinal number as a center and the search radius of the tomato inspection robot as a radius;

determining an eight neighborhood for the positive node and the negative node under the current iteration ordinal number based on relative positions of the positive node and the negative node under the current iteration ordinal number;

calculating a corresponding heuristic function value from each node in a positive target node set to the positive node under the current iteration ordinal number, as well as a corresponding heuristic function value from each node in a negative target node set to the negative node under the current iteration ordinal number based on the heuristic function under the current iteration ordinal number to obtain a positive heuristic function value set and a negative heuristic function value set, wherein the positive target node set comprises all nodes whose distances from the positive node under the current iteration ordinal number are greater than the positive safety distance in the eight neighborhood of the positive node under the current iteration ordinal number, and the negative target node set comprises all nodes whose distances from the negative node under the current iteration ordinal number are greater than the negative safety distance in the eight neighborhood of the negative node under the current iteration ordinal number;

determining a positive node and a negative node under a next iteration ordinal number based on the positive heuristic function value set and the negative heuristic function value set;

if there is no obstacle on a direct connection path between the positive node and the negative node under the next iteration ordinal number, performing backward tracing from the positive node under the next iteration ordinal number to the start point and from the negative node under the next iteration ordinal number to the end point to obtain a planned path, wherein the direct connection path is a path formed through direct connection; and if there is an obstacle on the direct connection path between the positive node and the negative node under the next iteration ordinal number, updating an iteration ordinal number, and entering a next iteration.

2. The path planning method for a tomato inspection robot according to claim 1, wherein the heuristic function is as follows:

$d=w1 \times d1 + w2 \times d2 + w3 \times 2.828 \times \min(dx,dy) + w4 \times 2.236 \times \min(dx,dy)$, wherein d represents the heuristic function value, d1 represents a diagonal distance between a $1^{st}$ node and a $2^{nd}$ node, d2 represents a Euclidean distance between the $1^{st}$ node and the $2^{nd}$ node, dx represents an absolute value of a difference between an abscissa of the $1^{st}$ node and an abscissa of the $2^{nd}$ node, dy represents an absolute value of a difference between an ordinate of the $1^{st}$ node and an ordinate of the $2^{nd}$ node, $\min(dx, dy)$ represents a minimum value between the dx and the dy, w1 represents a first weight, w2 represents a second weight, w3 represents a third weight, and w4 represents a fourth weight.

3. The path planning method for a tomato inspection robot according to claim 1, wherein the determining a positive safety distance based on whether there is an obstacle within a circle with the positive node under the current iteration ordinal number as a center and the search radius of the tomato inspection robot as a radius comprises:

if there is an obstacle within the circle with the positive node under the current iteration ordinal number as the center and the search radius of the tomato inspection robot as the radius, increasing the positive safety distance; or if there is no obstacle within the circle with the positive node under the current iteration ordinal number as the center and the search radius of the tomato inspection robot as the radius, decreasing the positive safety distance.

4. The path planning method for a tomato inspection robot according to claim 1, wherein the determining a negative safety distance based on whether there is an obstacle within a circle with the negative node under the current iteration ordinal number as a center and the search radius of the tomato inspection robot as a radius specifically comprises:

if there is an obstacle within the circle with the negative node under the current iteration ordinal number as the center and the search radius of the tomato inspection robot as the radius, increasing the negative safety distance; or if there is no obstacle within the circle with the negative node under the current iteration ordinal number as the center and the search radius of the tomato inspection robot as the radius, decreasing the negative safety distance.

5. The path planning method for a tomato inspection robot according to claim 1, wherein the determining an eight neighborhood for the positive node and the negative node under the current iteration ordinal number based on relative positions of the positive node and the negative node under the current iteration ordinal number specifically comprises:

establishing a positive coordinate system with the positive node under the current iteration ordinal number as an origin;

obtaining the eight neighborhood for the positive node under the current iteration ordinal number based on an eight neighborhood template corresponding to a quadrant in which the negative node under the current iteration ordinal number is located in the positive coordinate system;

establishing a negative coordinate system with the negative node under the current iteration ordinal number as an origin; and obtaining the eight neighborhood for the negative node under the current iteration ordinal number based on an eight neighborhood template corresponding to a quadrant in which the positive node under the current iteration ordinal number is located in the negative coordinate system.

6. The path planning method for a tomato inspection robot according to claim 1, wherein the performing backward tracing from the positive node under the next iteration ordinal number to the start point and from the negative node under the next iteration ordinal number to the end point to obtain a planned path specifically comprises:

performing the backward tracing from the positive node under the next iteration ordinal number to the start point and from the negative node under the next iteration ordinal number to the end point to obtain a preliminary path; and smoothing the preliminary path to obtain the planned path.

7. A path planning apparatus for a tomato inspection robot, comprising:

an obtaining module configured to obtain a 2D raster map of a tomato orchard, and determine start and end points in the 2D raster map and a search radius of the tomato inspection robot;

an updating module configured to: under a current iteration ordinal number, calculate a cost of a positive node under the current iteration ordinal number based on a heuristic function under a previous iteration ordinal number, and update a weight of the heuristic function under the previous iteration ordinal number based on the cost of the positive node under the current iteration ordinal number to obtain a heuristic function under the current iteration ordinal number, wherein the cost is a sum of a corresponding heuristic function value from the positive node under the current iteration ordinal number to a negative node under the current iteration ordinal number, a corresponding heuristic function value from the positive node under the current iteration ordinal number to the end point, and a corresponding heuristic function value from the positive node under the current iteration ordinal number to the start point; the heuristic function is a weighted sum of a Euclidean distance and a diagonal distance between two nodes; and a positive node under an initial iteration ordinal number is the start point, and a negative node under the initial iteration ordinal number is the end point;

a safety distance determining module configured to determine a positive safety distance based on whether there is an obstacle within a circle with the positive node under the current iteration ordinal number as a center and the search radius of the tomato inspection robot as a radius, and determine a negative safety distance based on whether there is an obstacle within a circle with the negative node under the current iteration ordinal number as a center and the search radius of the tomato inspection robot as a radius;

an eight neighborhood determining module configured to determine an eight neighborhood for the positive node and the negative node under the current iteration ordinal number based on relative positions of the positive node and the negative node under the current iteration ordinal number;

a heuristic function value set calculation module configured to: calculate a corresponding heuristic function value from each node in a positive target node set to the positive node under the current iteration ordinal number, as well as a corresponding heuristic function value from each node in a negative target node set to the negative node under the current iteration ordinal number based on the heuristic function under the current iteration ordinal number to obtain a positive heuristic function value set and a negative heuristic function value set, wherein the positive target node set comprises all nodes whose distances from the positive node under the current iteration ordinal number are greater than the positive safety distance in the eight neighborhood of the positive node under the current iteration ordinal number, and the negative target node set comprises all nodes whose distances from the negative node under the current iteration ordinal number are greater than the negative safety distance in the eight neighborhood of the negative node under the current iteration ordinal number;

a module for determining a node under a next iteration ordinal number configured to determine a positive node and a negative node under the next iteration ordinal number based on the positive heuristic function value set and the negative heuristic function value set;

a planned path determining module configured to: if there is no obstacle on a direct connection path between the positive node and the negative node under the next iteration ordinal number, perform backward tracing from the positive node under the next iteration ordinal number to the start point and from the negative node under the next iteration ordinal number to the end point to obtain a planned path, wherein the direct connection path is a path formed through direct connection; and an iteration module configured to: if there is an obstacle on the direct connection path between the positive node and the negative node under the next iteration ordinal number, update an iteration ordinal number, and enter a next iteration.

8. A computer device, comprising: a memory, a processor and a computer program stored in the memory and executable on the processor, wherein the processor executes the computer program to implement the path planning method for a tomato inspection robot according to claim 1.

9. A non-transitory computer-readable storage medium, wherein a computer program is stored thereon, and the computer program is executed by a processor to implement the path planning method for a tomato inspection robot according to claim 1.

10. The computer device according to claim 8, wherein the heuristic function is as follows:

$d=w1 \times d1 + w2 \times d2 + w3 \times 2.828 \times \min(dx, dy) + w4 \times 2.236 \times \min(dx, dy)$, wherein d represents the heuristic function value, d1 represents a diagonal distance between a $1^{st}$ node and a $2^{nd}$ node, d2 represents a Euclidean distance between the $1^{st}$ node and the $2^{nd}$ node, dx represents an absolute value of a difference between an abscissa of the $1^{st}$ node and an abscissa of the $2^{nd}$ node, dy represents an absolute value of a difference between an ordinate of the $1^{st}$ node and an ordinate of the $2^{nd}$ node, min(dx, dy) represents a minimum value between the dx and the dy, w1 represents a first weight, w2 represents a second weight, w3 represents a third weight, and w4 represents a fourth weight.

11. The computer device according to claim 8, wherein the determining a positive safety distance based on whether there is an obstacle within a circle with the positive node under the current iteration ordinal number as a center and the search radius of the tomato inspection robot as a radius comprises:

if there is an obstacle within the circle with the positive node under the current iteration ordinal number as the center and the search radius of the tomato inspection robot as the radius, increasing the positive safety distance; or if there is no obstacle within the circle with the positive node under the current iteration ordinal number as the center and the search radius of the tomato inspection robot as the radius, decreasing the positive safety distance.

12. The computer device according to claim 8, wherein the determining a negative safety distance based on whether there is an obstacle within a circle with the negative node under the current iteration ordinal number as a center and the search radius of the tomato inspection robot as a radius specifically comprises:

if there is an obstacle within the circle with the negative node under the current iteration ordinal number as the center and the search radius of the tomato inspection robot as the radius, increasing the negative safety distance; or if there is no obstacle within the circle with the negative node under the current iteration ordinal number as the center and the search radius of the tomato inspection robot as the radius, decreasing the negative safety distance.

13. The computer device according to claim 8, wherein the determining an eight neighborhood for the positive node and the negative node under the current iteration ordinal number based on relative positions of the positive node and the negative node under the current iteration ordinal number specifically comprises:

establishing a positive coordinate system with the positive node under the current iteration ordinal number as an origin;

obtaining the eight neighborhood for the positive node under the current iteration ordinal number based on an eight neighborhood template corresponding to a quadrant in which the negative node under the current iteration ordinal number is located in the positive coordinate system;

establishing a negative coordinate system with the negative node under the current iteration ordinal number as an origin; and obtaining the eight neighborhood for the negative node under the current iteration ordinal number based on an eight neighborhood template corresponding to a quadrant in which the positive node under the current iteration ordinal number is located in the negative coordinate system.

14. The computer device according to claim 8, wherein the performing backward tracing from the positive node under the next iteration ordinal number to the start point and from the negative node under the next iteration ordinal number to the end point to obtain a planned path specifically comprises:

performing the backward tracing from the positive node under the next iteration ordinal number to the start point and from the negative node under the next iteration ordinal number to the end point to obtain a preliminary path; and smoothing the preliminary path to obtain the planned path.

15. The non-transitory computer-readable storage medium according to claim 9, wherein the heuristic function is as follows:

$d=w1\times d1+w2\times d2+w3\times2.828\times\min(dx,dy)+w4\times2.236\times\min(dx,dy)$, wherein d represents the heuristic function value, d1 represents a diagonal distance between a $1^{st}$ node and a $2^{nd}$ node, d2 represents a Euclidean distance between the $1^{st}$ node and the $2^{nd}$ node, dx represents an absolute value of a difference between an abscissa of the $1^{st}$ node and an abscissa of the $2^{nd}$ node, dy represents an absolute value of a difference between an ordinate of the $1^{st}$ node and an ordinate of the $2^{nd}$ node, min(dx, dy) represents a minimum value between the dx and the dy, w1 represents a first weight, w2 represents a second weight, w3 represents a third weight, and w4 represents a fourth weight.

16. The non-transitory computer-readable storage medium according to claim 9, wherein the determining a positive safety distance based on whether there is an obstacle within a circle with the positive node under the current iteration ordinal number as a center and the search radius of the tomato inspection robot as a radius comprises:

if there is an obstacle within the circle with the positive node under the current iteration ordinal number as the center and the search radius of the tomato inspection robot as the radius, increasing the positive safety distance; or if there is no obstacle within the circle with the positive node under the current iteration ordinal number as the center and the search radius of the tomato inspection robot as the radius, decreasing the positive safety distance.

17. The non-transitory computer-readable storage medium according to claim 9, wherein the determining a negative safety distance based on whether there is an obstacle within a circle with the negative node under the current iteration ordinal number as a center and the search radius of the tomato inspection robot as a radius specifically comprises:

if there is an obstacle within the circle with the negative node under the current iteration ordinal number as the center and the search radius of the tomato inspection robot as the radius, increasing the negative safety distance; or if there is no obstacle within the circle with the negative node under the current iteration ordinal number as the center and the search radius of the tomato inspection robot as the radius, decreasing the negative safety distance.

18. The non-transitory computer-readable storage medium according to claim 9, wherein the determining an eight neighborhood for the positive node and the negative node under the current iteration ordinal number based on relative positions of the positive node and the negative node under the current iteration ordinal number specifically comprises:

establishing a positive coordinate system with the positive node under the current iteration ordinal number as an origin;

obtaining the eight neighborhood for the positive node under the current iteration ordinal number based on an eight neighborhood template corresponding to a quadrant in which the negative node under the current iteration ordinal number is located in the positive coordinate system;

establishing a negative coordinate system with the negative node under the current iteration ordinal number as an origin; and obtaining the eight neighborhood for the negative node under the current iteration ordinal number based on an eight neighborhood template corresponding to a quadrant in which the positive node under the current iteration ordinal number is located in the negative coordinate system.

19. The non-transitory computer-readable storage medium according to claim 9, wherein the performing backward tracing from the positive node under the next iteration ordinal number to the start point and from the negative node under the next iteration ordinal number to the end point to obtain a planned path specifically comprises:

performing the backward tracing from the positive node under the next iteration ordinal number to the start point and from the negative node under the next iteration ordinal number to the end point to obtain a preliminary path; and smoothing the preliminary path to obtain the planned path.

\* \* \* \* \*